US009467553B2

(12) United States Patent
Heo et al.

(10) Patent No.: US 9,467,553 B2
(45) Date of Patent: Oct. 11, 2016

(54) MOBILE TERMINAL AND METHOD OF CONTROLLING THE SAME

(71) Applicant: LG ELECTRONICS INC., Seoul (KR)

(72) Inventors: Jeongyun Heo, Seoul (KR); Hoyoul Park, Seoul (KR); Chankwon Kim, Seoul (KR); Wonsuk Kang, Seoul (KR); Jeongjae Lee, Seoul (KR); Jiyong Yoo, Seoul (KR); Minsuk Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 14/507,112

(22) Filed: Oct. 6, 2014

(65) Prior Publication Data
US 2015/0215443 A1 Jul. 30, 2015

(30) Foreign Application Priority Data

Jan. 24, 2014 (KR) ........................ 10-2014-0009105

(51) Int. Cl.
| H04M 1/00 | (2006.01) |
| H04M 1/725 | (2006.01) |
| A61B 5/00 | (2006.01) |
| G06F 1/16 | (2006.01) |
| H04B 1/3827 | (2015.01) |
| H04M 1/05 | (2006.01) |
| H04M 1/02 | (2006.01) |
| G08B 25/00 | (2006.01) |
| G08B 25/01 | (2006.01) |
(Continued)

(52) U.S. Cl.
CPC .......... *H04M 1/72569* (2013.01); *A61B 5/681* (2013.01); *A61B 5/6824* (2013.01); *G06F 1/163* (2013.01); *G08B 25/001* (2013.01); *G08B 25/016* (2013.01); *H04B 1/3827* (2013.01); *H04M 1/0202* (2013.01); *H04M 1/05* (2013.01); *H04M 1/7253* (2013.01); *H04B 2001/3861* (2013.01); *H04M 2250/12* (2013.01)

(58) Field of Classification Search
None
See application file for complete search history.

(56) References Cited

U.S. PATENT DOCUMENTS

| 6,244,873 B1 * | 6/2001 | Hill | .................. G06F 3/015 379/110.01 |
| 7,102,507 B1 * | 9/2006 | Lauren | ............... G07C 9/00182 340/12.55 |
| 2010/0124949 A1 * | 5/2010 | Demuynck | ........... G06F 1/1626 455/569.1 |
| 2012/0046009 A1 * | 2/2012 | Persson | .................. A42B 3/046 455/404.2 |
| 2014/0055352 A1 * | 2/2014 | Davis | ..................... G06F 3/017 345/156 |

FOREIGN PATENT DOCUMENTS

| CH | 697 402 B1 | 9/2008 | |
| CH | 697402 B1 * | 9/2008 | ........... A61B 5/1117 |
| EP | 2 424 196 A1 | 2/2012 | |

OTHER PUBLICATIONS

European Search Report issued in Application No. 14192792.1 dated Jun. 16, 2015.

* cited by examiner

*Primary Examiner* — Mohammed Rachedine
(74) *Attorney, Agent, or Firm* — Ked & Associates, LLP

(57) ABSTRACT

Provided is a mobile terminal including a main body, a sensing unit that senses wearing of the main body, movement information on a wearer, and a biological signal of the wearer, a user input unit into which a control command is input for activating either a recording mode or a control mode when the wearing of the main body is sensed, and a controller that, in the recording mode, records the movement information and the biological signal in a specific situation and stores a movement pattern that occurs in the specific situation and which, in the control mode, senses the movement information and the biological signal and when the already-stored movement pattern in the specific situation that corresponds to the movement information and the biological signal that are sensed is detected, provides a control command corresponding to the detected movement pattern to a connected external device.

20 Claims, 24 Drawing Sheets

100

100
200

(a)

(b)

(c)

(d)

(e)

(f)

(g)

(h)

MOBILE TERMINAL AND METHOD OF CONTROLLING THE SAME

CROSS-REFERENCE TO RELATED APPLICATION

Pursuant to 35 U.S.C. §119(a), this application claims the benefit of earlier filing date and right of priority to Korean Application No. 10-2014-0009105, filed on Jan. 24, 2014, the contents of which is incorporated by reference herein in its entirety.

BACKGROUND

1. Field

The present disclosure relates to a mobile terminal that is wearable on a portion of a user's body and a method of controlling the mobile terminal.

2. Background

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

Efforts are ongoing to support and increase the functionality of mobile terminals. Such efforts include software and hardware improvements, as well as changes and improvements in the structural components.

Thanks to these improvements, the terminals have evolved into various types of designs. Specifically, making the terminals more lightweight and more minimized has made it possible to realize terminals that are capable of being worn on a portion of a user's body, such as a glasses-type terminal, a watch-type terminal, a necklace-type terminal, a bracelet-type terminal, and a ring-type terminal. Furthermore, terminals that are capable of being attached to clothes are also under development. When such terminals are worn on any portion of the user's body in order to be used according to a user's purpose and intention, a movement and biological signal of the wearer can be detected and accordingly various functions can be performed.

The above references are incorporated by reference herein where appropriate for appropriate teachings of additional or alternative details, features and/or technical background.

SUMMARY OF THE DISCLOSURE

Therefore, an aspect of the detailed description is to provide a mobile terminal that is capable of detecting and recording a movement and biological signal of a user who wears a main body thereof in a specific situation and of using recorded information to perform a specific function when the same situation occurs thereafter, and a method of controlling the mobile terminal.

An another aspect of the detailed description is to a mobile terminal that is capable of storing a movement of a wearer and a pattern of a biological signal of the wearer that are recorded in a specific situation and of controlling at least one external device associated with the specific situation when the movement and biological signal that are the same as the recorded pattern are detected, and a method of controlling the mobile terminal.

A further aspect of the detailed description is to provide a mobile terminal that is capable of detecting a movement of a user who wears a main body thereof and a biological signal of the user and of displaying an image associated with the recognized gesture, and a method of controlling the mobile terminal.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWINGS

The embodiments will be described in detail with reference to the following drawings in which like reference numerals refer to like elements wherein.

DETAILED DESCRIPTION

Figure 1A:
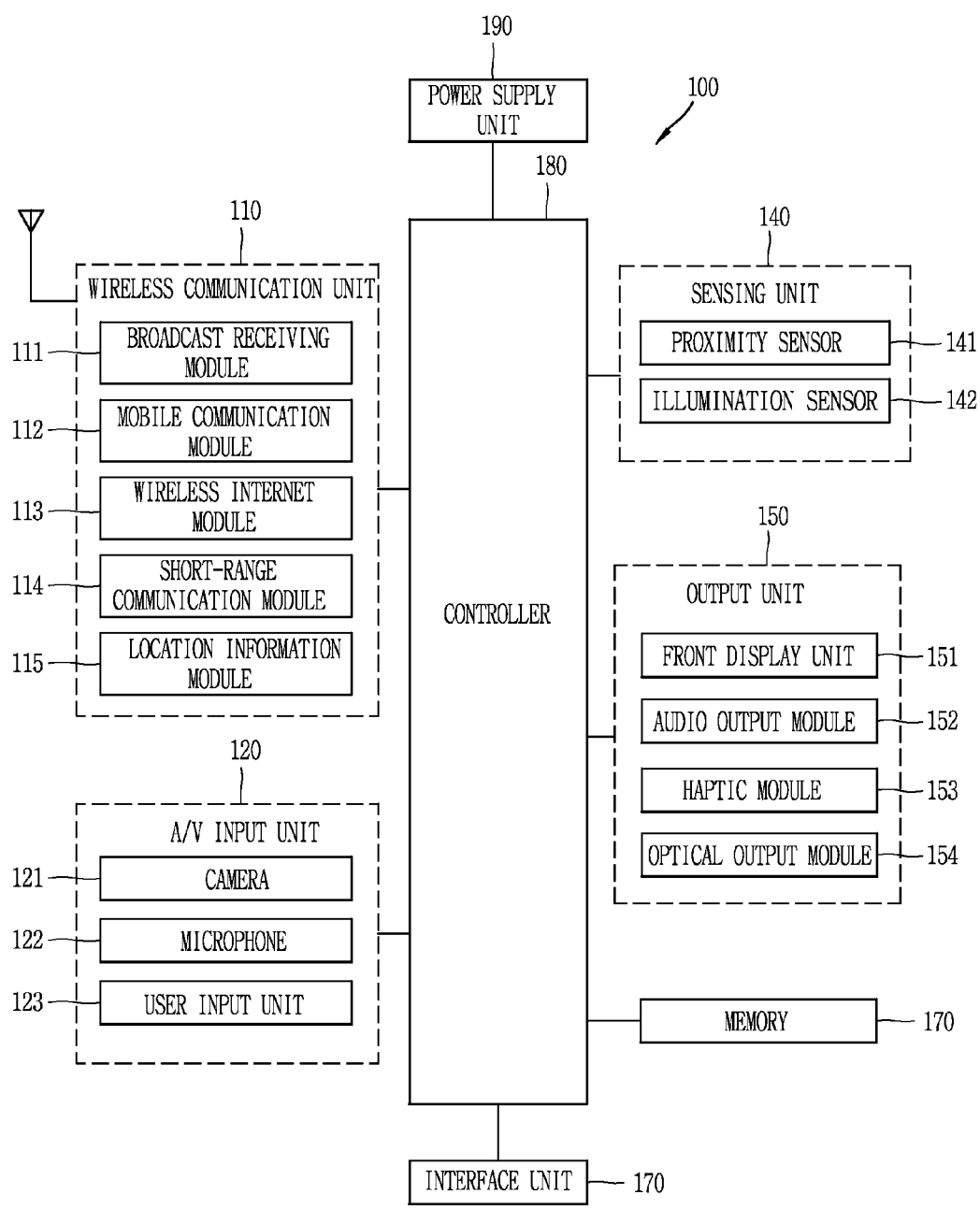
FIG. 1A is a block diagram for describing a mobile terminal according to the present disclosure.

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1B:
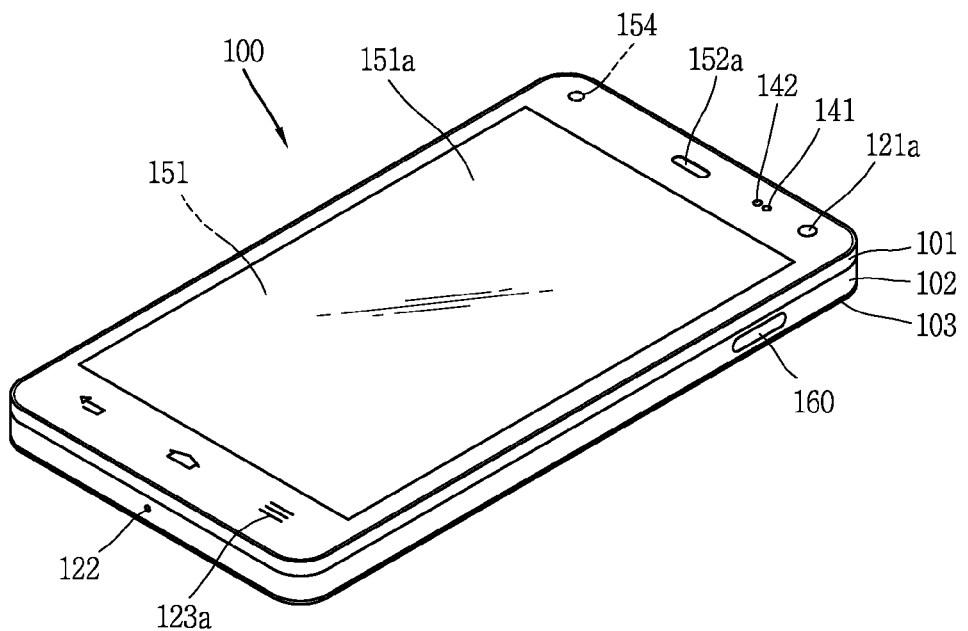
FIGS. 1B and 1C are diagrams illustrating the mobile terminal according to the present disclosure when viewed from different directions.
Figure 1C:
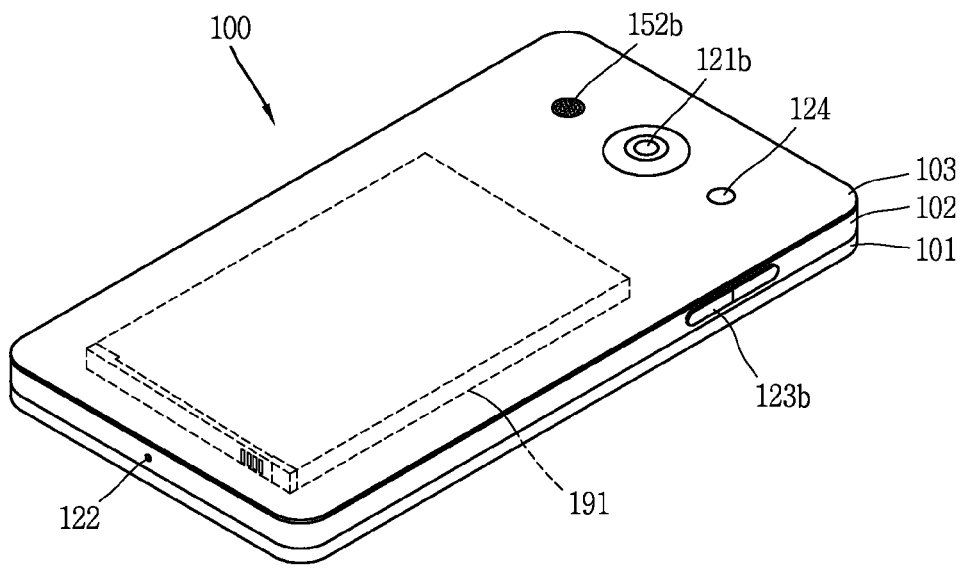

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

Referring now to FIG. 1A, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the various components depicted in FIG. 1A, or activating application programs stored in the memory 170. As one example, the controller 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Referring still to FIG. 1A, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like).

Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The user input unit 123 may recognize information sensed by the sensing unit 140, as well as by the aforementioned mechanical input means and touch type input means, as information input from a user. Accordingly, the controller 180 can control an operation of the mobile terminal 100 corresponding to the sensed information.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

A projection unit 155 is arranged in an arbitrary portion of the mobile terminal 100. The projection unit 155 includes a light source element, an image formation module, and a lens. The projection unit 155 is configured to project image information. In addition, at this point, the light source element emits light, and the image formation module forms the image information (or screen information) using the light. The lens is for projecting the image information in a magnified manner and is arranged in such a manner as to correspond to a projection hole. In addition, the projection unit 155 is referred to as a cineprojector, a projection, or a beam projector.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like.

As an alternative to the example in which the plurality of cases form an inner space for accommodating components, the mobile terminal 100 may be configured such that one case forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

FIGS. 1B and 1C depict certain components as arranged on the mobile terminal. However, it is to be understood that alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a.

The first audio output module 152a may be implemented in the form of a speaker to output voice audio, alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151a and the front case 101). In this case, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 154 to stop the light output.

The first camera 121a can process image frames such as still or moving images obtained by the image sensor in a capture mode or a video call mode. The processed image frames can then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 1B illustrates the first manipulation unit 123a as a touch key, but possible alternatives include a mechanical key, a push key, a touch key, and combinations thereof.

Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit (not shown) may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123a in the rear input unit. As such, in situations where the first manipulation unit 123a is omitted from the front side, the display unit 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

As shown in FIG. 1C, a flash 124 is shown adjacent to the second camera 121b. When an image of a subject is captured with the camera 121b, the flash 124 may illuminate the subject.

As shown in FIG. 1B, the second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

Hereinafter, a communication system which is operable with the display device 100 according to the present disclosure will be described.

A communication system which is operable with the variously described mobile terminals will now be described in more detail. Such a communication system may be configured to utilize any of a variety of different air interfaces and/or physical layers. Examples of such air interfaces utilized by the communication system include Frequency Division Multiple Access (FDMA), Time Division Multiple Access (TDMA), Code Division Multiple Access (CDMA), Universal Mobile Telecommunications System (UMTS) (including, Long Term Evolution (LTE), LTE-A (Long Term Evolution-Advanced)), Global System for Mobile Communications (GSM), and the like.

By way of a non-limiting example only, further description will relate to a CDMA communication system, but such teachings apply equally to other system types including a CDMA wireless communication system as well as OFDM (Orthogonal Frequency Division Multiplexing) wireless communication system. A CDMA wireless communication system generally includes one or more mobile terminals (MT or User Equipment, UE) 100, one or more base stations (BSs, NodeB, or evolved NodeB), one or more base station controllers (BSCs), and a mobile switching center (MSC). The MSC is configured to interface with a conventional Public Switched Telephone Network (PSTN) and the BSCs. The BSCs are coupled to the base stations via backhaul lines. The backhaul lines may be configured in accordance with any of several known interfaces including, for example, E1/T1, ATM, IP, PPP, Frame Relay, HDSL, ADSL, or xDSL. Hence, the plurality of BSCs can be included in the CDMA wireless communication system.

Each base station may include one or more sectors, each sector having an omni-directional antenna or an antenna pointed in a particular direction radially away from the base station. Alternatively, each sector may include two or more different antennas. Each base station may be configured to support a plurality of frequency assignments, with each frequency assignment having a particular spectrum (e.g., 1.25 MHz, 5 MHz, etc.).

The intersection of sector and frequency assignment may be referred to as a CDMA channel. The base stations may also be referred to as Base Station Transceiver Subsystems (BTSs). In some cases, the term "base station" may be used to refer collectively to a BSC, and one or more base stations.

The base stations may also be denoted as "cell sites." Alternatively, individual sectors of a given base station may be referred to as cell sites.

A broadcasting transmitter (BT) transmits a broadcast signal to the mobile terminals 100 operating within the system. The broadcast receiving module 111 of FIG. 1A is typically configured inside the mobile terminal 100 to receive broadcast signals transmitted by the BT.

Global Positioning System (GPS) satellites for locating the position of the mobile terminal 100, for example, may cooperate with the CDMA wireless communication system. Useful position information may be obtained with greater or fewer satellites than two satellites. It is to be appreciated that other types of position detection technology, (i.e., location technology that may be used in addition to or instead of GPS location technology) may alternatively be implemented. If desired, at least one of the GPS satellites may alternatively or additionally be configured to provide satellite DMB transmissions.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

Figure 2:
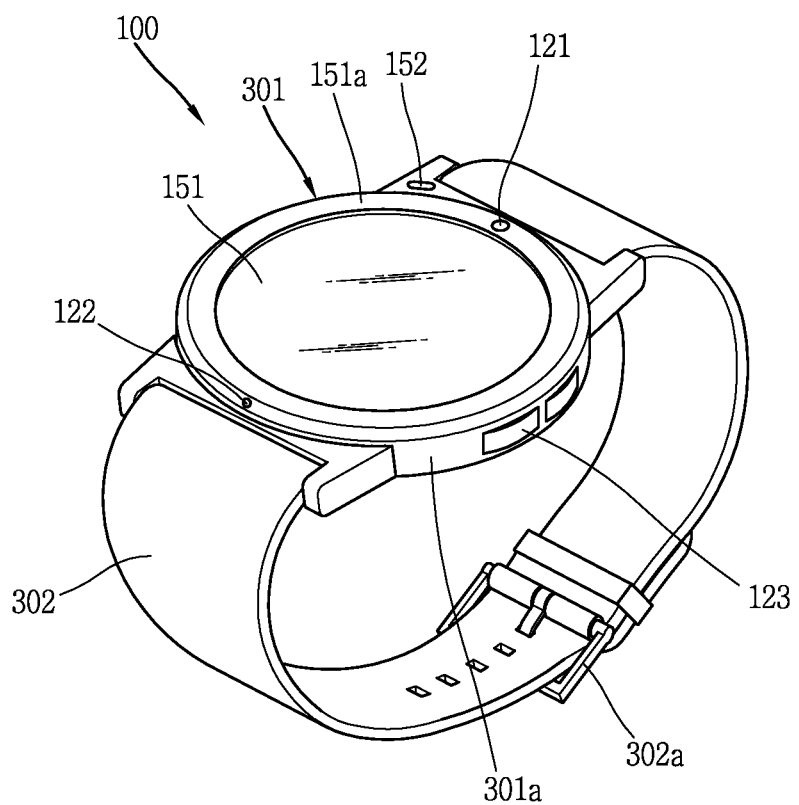
FIG. 2 is a perspective diagram illustrating one example of a watch-type mobile terminal according to another embodiment of the present disclosure.

FIG. 2 is a perspective view illustrating one example of a watch-type mobile terminal 100 in accordance with another exemplary embodiment.

As illustrated in FIG. 2, the watch-type mobile terminal 100 includes a main body 301 with a display unit 151 and a band 302 connected to the main body 301 to be wearable on a wrist. In general, mobile terminal 100 may be configured to include features that are the same or similar to that of mobile terminal 100 of FIGS. 1A-1C.

The main body 301 may include a case having a certain appearance. As illustrated, the case may include a first case 301a and a second case 301b cooperatively defining an inner space for accommodating various electronic components. Other configurations are possible. For instance, a single case may alternatively be implemented, with such a case being configured to define the inner space, thereby implementing a mobile terminal 100 with a uni-body.

The watch-type mobile terminal 100 can perform wireless communication, and an antenna for the wireless communication can be installed in the main body 301. The antenna may extend its function using the case. For example, a case including a conductive material may be electrically connected to the antenna to extend a ground area or a radiation area.

The display unit 151 is shown located at the front side of the main body 301 so that displayed information is viewable to a user. In some embodiments, the display unit 151 includes a touch sensor so that the display unit can function as a touch screen. As illustrated, window 151a is positioned on the first case 301a to form a front surface of the terminal body together with the first case 301a.

The illustrated embodiment includes an audio output module 152, a camera 121, a microphone 122, and a user input unit 123 positioned on the main body 301. When the display unit 151 is implemented as a touch screen, additional function keys may be minimized or eliminated. For example, when the touch screen is implemented, the user input unit 123 may be omitted. In addition, the projection unit (not illustrated) may be further included in a main body 301. Although not illustrated, the projection unit includes the light source element, the image formation module and the lens. At this point, the light source element emits light, and the image formation module forms the image information (or the screen information) using the light. The lens is for projecting the image information in a magnified manner and is arranged in such a manner as to correspond to the projection hole. The projection unit (not illustrated) is referred to the cineprojector, the projector, or the beam projector. The projection unit is arranged on a lateral surface of the mobile terminal main body 301, but is not limited to the side and may be arranged in an arbitrary portion of the main body 301.

The band 302 is commonly worn on the user's wrist and may be made of a flexible material for facilitating wearing of the device. As one example, the band 302 may be made of fur, rubber, silicon, synthetic resin, or the like. The band 302 may also be configured to be detachable from the main body 301. Accordingly, the band 302 may be replaceable with various types of bands according to a user's preference.

In one configuration, the band 302 may be used for extending the performance of the antenna. For example, the band may include therein a ground extending portion (not shown) electrically connected to the antenna to extend a ground area.

The band 302 may include fastener 302a. The fastener 302a may be implemented into a buckle type, a snap-fit hook structure, a Velcro® type, or the like, and include a flexible section or material. The drawing illustrates an example that the fastener 302a is implemented using a buckle.

The mobile terminal 100 according to an embodiment of the present disclosure, which is capable of being worn on a specific body portion and which is configured to include at least one among the constituent elements described above, for example, a watch-type mobile terminal 100 detects movement information on a wearer of the main body 301 and a biological signal of the wearer, through the sensing unit 140.

At this point, the movement information on the wearer means a gesture that is performed using a wearer's finger, wrist, shoulder, head, leg, or waist. The movement information on the wearer is obtained by analyzing the image information captured with the motion sensor, the geomagnetic sensor, the acceleration sensor and the gyro sensor, which are included in the sensing unit 140, and with the camera 121.

In addition, at this point, the biological signal means an electric signal that is generated in the body of the wearer of the mobile terminal 100. For example, the biological signal is any of an electrocardiogram (ECG) signal, a photoplethymogram signal, and galvanic skin response signal, but is not limited to these and may include various types of signals that, in the related art, are in wide use for measurements during sleeping.

More specifically, major electric measurements of the wearer's body include an electroencephalogram, an electrocardiogram, an electromyogram, eyeball conductivity, and electric skin reaction. Major physical measurements include blood pressure, a heart rate, an allorhythmic pulse, a stroke quotient, a stroke defect, body temperature, and a breathing rate. The sensing unit 140 detects at least one or more among the major electric measurements and the major physical measurements.

The electrocardiogram (ECG) signal is an electric signal that is generated on the surface of a skin in which a heart's electric activity occurs. The ECG signal is measured by inducing active electric current, which occurs in heart muscles according to heart beats, into two suitable areas on the surface of the body.

An electromyogram (EMG) signal is an electric signal that is generated on the surface of a skin in which muscle contraction, muscle activity, and muscle fatigue degree occur. The EMG detects muscle movement according to the movement of the wearer's finger that is sensed by wearing the watch-type mobile terminal 300. Specifically, a carpal tunnel within the wrist of the wearer of the mobile terminal has finger flexor tendons of muscles that control movements of fingers. The finger flexor tendons have 9 tendons and one nerve, and if the finger moves, the 9 tendons included in the finger flexor tendons are variously combined to move. The sensing unit 140 of the mobile terminal detects shapes of the tendons that are changed according to the movement of the fingers or the movement of the wrist, and the controller 180 determines what gesture is performed with the fingers, based on the sensed information.

An electroencephalogram (EEG) signal is an electric signal that is generated on the surface of a skin in which concentration or brain activity in response to an external stimulus occurs. The EEG signal is measured by inducing into a scalp a change in electric potential that occurs in a human cerebrum, or brain electric current resulting from the change.

A galvanic skin reflex (GSR) signal is an electric signal that generated on the surface of a skin in which a change in skin resistance to activity of a sympathetic nerve occurs. The GSR signal is obtained by measuring a phenomenon in which electric resistance that occurs in the skin of the living body due to an external stimulus or emotional excitement is decreased temporarily or the active electric potential occurs.

When the sensing unit 140 detects the wearing of the watch-type mobile terminal 300, a control command that allows the controller 180 to activate either a recording mode or a control mode, is input into the user input unit 123.

At this point, the control command, as described above, is input through a mechanical input unit or a touch input unit. However, without these, pieces of information that are sensed through the sensing unit 140 are received and recognized as being input from the user.

When the recording mode is activated, the controller 180 records the movement information on the wearer of the main body 301 and stores a movement pattern that occurs in a specific situation. For example, the controller 180 of the mobile terminal 100 records the movement information on the wearer and the biological signal of the wearer that occurs in a situation where the wearer performs an operation of opening a trunk of his/her car.

On the other hand, when the control mode is activated, the controller 180 senses the movement information on the wearer and the biological signal of the wearer. Then, the movement pattern that corresponds to the sensed movement information and biological signal and which is stored in the specific situation is detected, the controller 180 provides a control command corresponding to the detected movement information to an external device connected.

On the other hand, when the movement information on the wearer and the biological signal of the wearer are different from those previously recorded and thus the movement pattern that occurs in a specific situation is changed, in the recording mode, the controller 180 updates the previous movement pattern with the changed movement pattern. That is, if the user's habitual gesture that is performed in a specific situation is changed, the update to the changed gesture is automatically performed, and thus operation of the external device can be controlled with the changed gesture.

As described above, the mobile terminal 100 according to the embodiment of the present disclosure can control the operation of the external device only with the wearer's habitual gesture without direct contact with the external device and without performing specific inputting on the mobile terminal 100. This provides the user with convenience.

A method of controlling the mobile terminal according to the embodiment of the present disclosure is described in detail below referring to FIG. 3.

First, the mobile terminal 100 according to the embodiment of the present disclosure is configured in such a manner that it can be worn on a specific body portion, and for example, is realized as the watch-type mobile terminal 100 illustrated in FIG. 2. The mobile terminal 100 according to the embodiment of the present disclosure is described below with the watch-type mobile terminal being as an example thereof.

First, the sensing unit 140 of the mobile terminal 100 performs a step of sensing the wearing of the main body (S310).

Specifically, the sensing unit 140 senses an inclination and a movement of the main body 310 of the mobile terminal 100 and thus senses whether or not the main body is worn. When a change in the inclination of the main body 301 and acceleration at which the main body 301 is moved are the same as or similar to the pattern that results when the main body 301 is moved worn on the body, the controller 180 determines that the main body 301 is worn on a portion of the user's body. To do this, the sensing unit 140 may further include a gyro sensor (not illustrated) that can sense a spatial movement with respect to an X-axis, an Y-axis, and a Z-axis.

In addition, based on the image information that is captured with the camera 121, the sensing unit 140 recognizes a position of the user and a worn state of the main body 301 of the mobile terminal 100. Accordingly, it can be determined whether the main body is worn on a portion of the user's body or is detached or moved away from the user.

In addition, according to how fastener 302*a* included in a band 302 of the main body 301 is connected to the band 302, the sensing unit 140 determines whether or not the mobile terminal 100 is worn on the body. That is, when it is determined that the fastener 302*a* is connected to one end of the band 302, the main body 301 is recognized as being worn on the body.

In addition, when after wearing the main body, the user pushes on a specific key or inputs a predetermined voice command, the sensing unit 140 senses the wearing of the main body.

On the other hand, the sensing unit 140 senses the wearing of the main body and at the same time or thereafter, senses the biological signal of the wearer of the main body 301, for example, a user's own heart rate. Then, the sensing 140 transfers the sensed biological signal to the controller 180 that performs user authentication. That is, according to the wearing of the main body 301, the user authentication is performed in a natural manner. On the other hand, when as a result of the user authentication, the wearer of the main body 301 is not matched with the already-stored user information, the mobile terminal 100 maintains a locked state in which the input of the control command to the mobile terminal 100 is limited, and outputs information corresponding to a failure of the user authentication.

When the wearing of the main body 301 is sensed in this manner, the controller 180 performs either the recording mode or the recording mode.

To do this, when the wearing of the main body 301 is sensed, the mobile terminal 100 performs a step of sensing the input of the control command for activating either the recording mode or the control mode through the user input unit 123 (S320).

When a specific first input signal is input through the user input unit 123 and then the movement information on the wearer of the main body and the biological signal of the wearer are sensed, the controller 180 recognizes that a control command for activating the recording mode in a specific situation corresponding to the first input signal.

At this point, the first input signal is one among a voice command to enter the recording mode in a specific situation, a specific key operation, and a specific gesture. In addition, the first input signal means a sensing signal according to a contact between the wearer of the main body 301 and a specific external device. For example, referring to FIG. 4B, the mobile terminal 100 senses the biological signal that occurs when a hand of the wearer comes into contact with a door knob, and based on the biological signal that is sensed at this time, recognizes that the first input signal for activating the recording mode in a "situation of opening a door" is input.

In addition, the motion information on the wearer means a gesture that is performed using a wearer's finger, wrist, shoulder, head, leg, or waist. The movement information on the wearer is obtained by analyzing the image information captured with the motion sensor, the geomagnetic sensor, the acceleration sensor and the gyro sensor, which are included in the sensing unit 140, and with the camera 121.

In addition, at this point, the biological signal of the wearer means an electric signal that is generated in the body of the wearer. For example, the biological signal includes the electrocardiogram (ECG), the photoplethymogram (PPG) signal, the galvanic skin response (GSR) signal and the electromyogram (EMG) signal.

In addition, the controller 180 recognizes the specific situation, based on at least one piece of information, among the first input signal described above, the piece of ambient image information that is obtained with the camera 121 arranged in the main body 301, and a piece of position information on the main body 301 that is received through the wireless communication unit 110. For example, when the first input signal corresponding to a voice "running" that is input through the microphone 122 is received, the controller 180 recognizes that a specific situation is "running."

On the other hand, when the sensing unit 140 directly senses the movement information on the wearer of the main body 301 and the biological signal of the wearer through the user input unit 123, the controller 180 recognizes this as the input of the control command for activating the control mode. In addition, when the sensing unit 140 senses the movement information on the wearer and the biological signal of the wearer that exceed a reference value (a value of a normal movement), the controller 180 generates the control command for activating the control mode and provide the generated control command to the user input unit 123.

Subsequently, the recording mode is activated, the controller 180 records the movement information on the wearer of the main body 301 and the biological signal of the wearer in a specific situation, and stores the movement pattern of the wearer that occurs in the specific situation (S330).

While the recording mode is activated in this manner, the sensing unit 140 senses the movement information on the wearer and the biological signal of the wearer.

The sensing unit 140 senses, for example, muscles that are changed according to movements of fingers of the wearer, shapes of tendons, a change in grip strength, and a finger's moving speed, through the electromyogram (EMG). The electromyogram (EMG) sensor senses electric activity of the muscles, and more specifically, senses an electric change within the muscles, thereby grasping a response to a nerve stimulus. Because the muscles are under the control of the nervous system and an infinitesimal amount of electric current always flows in the muscle, if the amount of electric current is checked with a needle or an electrode and is recorded with an electromyograph, the activity of the muscle including peripheral nerves can be grasped.

In addition, the sensing unit 140 transfers results of sensing the changed muscles, the shapes of tendons, the change in grip strength, and the finger's moving speed to the controller 180. The controller 180 grasps a movement characteristic.

The movement characteristic is about at least one among the shapes of fingers (or the gestures), the finger's moving speed, the direction of a wrist movement, the wrist's moving speed, and the change in grip strength. In addition, the movement characteristic changes variously with the finger movement or the wrist movement. For example, the movement characteristic that results when five fingers are unfolded is different from one that results when the five fingers are folded. This is because the movements and the shapes of the tendons differ with the movements of the fingers.

Figure 5:
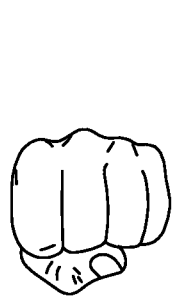
FIG. 5 is diagram, each illustrating an example of a hand gesture of a wearer that provides a different biological signal to the mobile terminal according to the embodiment of the present disclosure.
Figure 5:
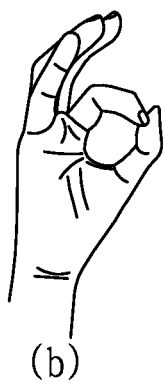
Figure 5:
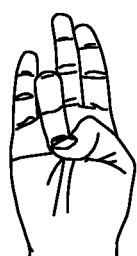
Figure 5:
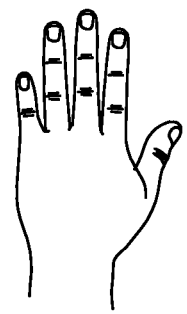
Figure 5:
Figure 5:
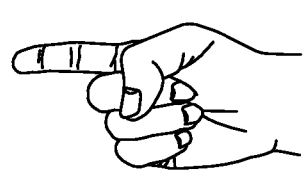
Figure 5:
Figure 5:

In association with this, FIG. 5 is a diagram, each illustrating an example of a gesture that is performed with the five fingers of the wearer and which provides a different biological signal to the mobile terminal 100. As illustrated in FIG. 5, in addition to when fingers of the wearer are unfolded and fingers are folded, a different electric signal occur when specific fingers are unfolded and specific fingers are folded, when multiple fingers comes into contact with one another, or when specific fingers point to a specific direction. Accordingly, electric waveforms that are generated when the wearer of the main body 301 throws his/her strength into his/her fingers are sensed through the electromyogram (EMG) sensor and thus five gestures illustrated in FIG. 5 are recognized as being distinguished from one another.

In addition, for example, through the electrocardiogram (ECG) sensor and/or the eletroencephalogram (EEG) sensor, the sensing unit 140 grasps whether the wearer is in a sleep state, in an awakened state, in an NRdEM (xoNon-REM) state, or in an awakening-suitable REM sleep state. Then, if as a result of the sensing, the awakened state is changed to the sleep state or the sleep state is changed to the awakened state, the first input signal is determined as being input and thus the recording mode described above is activated.

On the other hand, when the control mode is activated, the controller 180 senses the movement information on the wearer and the biological signal of the wearer, and when the already-stored movement pattern in a specific situation that corresponds to the sensed movement information and biological signal is detected, performs a step of providing the control command corresponding to the detected movement pattern to the external device (S340).

In addition, in the control mode, when the already-stored movement pattern in the specific situation that corresponds to the sensed movement information and biological signal is detected, the controller 180 remotely control the operation of the connected external device according to the control command that corresponds to the detected movement pattern. A result of the remote control is received back in the mobile terminal 100.

To do this, the wireless communication unit 110 of the mobile terminal 100 is connected to the external device and transmits the control command corresponding to the detected movement pattern using wireless communication technologies, such as Wireless LAN (WLAN), Bluetooth, Ultra Wide Band band (UWB), Infrared Data Association (IrDA), Home Phoneline Networking Alliance (HPNA), Shared Wireless Access Protocol (SWAP), and IEEE 1394.

On the other hand, in the control mode, when the already-stored movement pattern in the specific situation that corresponds to the sensed movement information and biological signal is not detected, the controller 180 outputs a message guiding the user through the entering of the recording mode.

There is no limit to types of external devices that can be connected to the mobile terminal 100. That is, whatever device can perform a specific function according to the control command that is received through the wireless communication unit 110 of the external device may be such an external device. For example, the external device includes not only home appliances, such as a refrigerator, a smart TV, a PC, a washing machine, lighting equipment, and a microwave oven, but also devices that are configured to receive the control signal from the mobile terminal 100, such as a vehicle, a front door, and an entrance door, and a main entrance.

In addition, the mobile terminal 100 outputs to the display unit 151 the screen information corresponding to the specific situation, in the recording mode or the control mode. For example, if the movement information and the biological signal corresponding to "golf motion" is recorded in the recording mode, the controller 180 outputs to the display unit 151 an image associated with "golf motion" while performing the recording.

Figure 3:
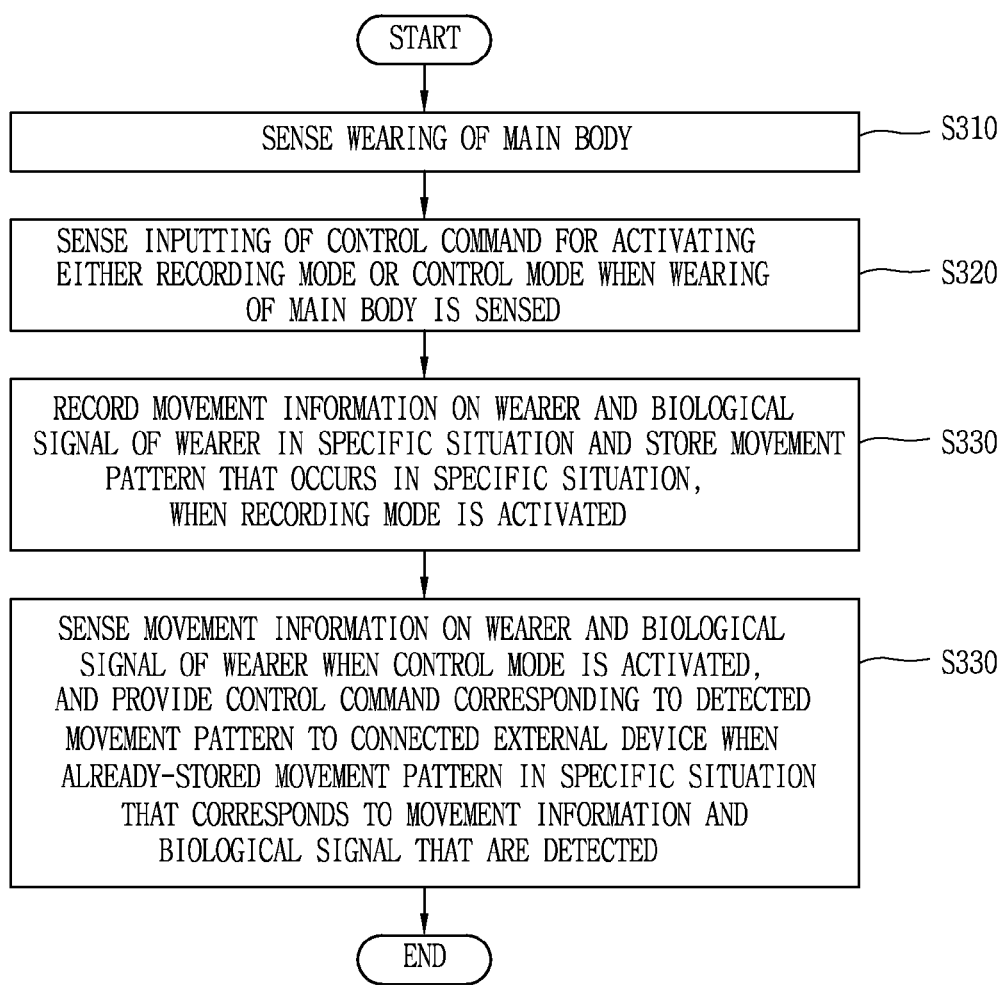
FIG. 3 is a flow chart for describing a method of controlling the mobile terminal according to an embodiment of the present disclosure.

FIGS. 4A to 4E are diagrams illustrating specific examples in the steps in FIG. 3, described above.

Figure 4A:
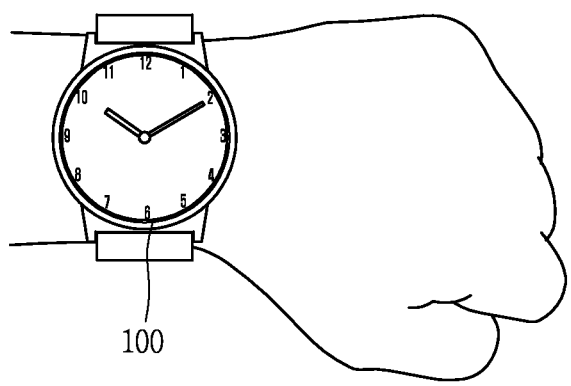
FIGS. 4A to 4E are diagrams for describing the flow chart in FIG. 3.
Figure 4B:
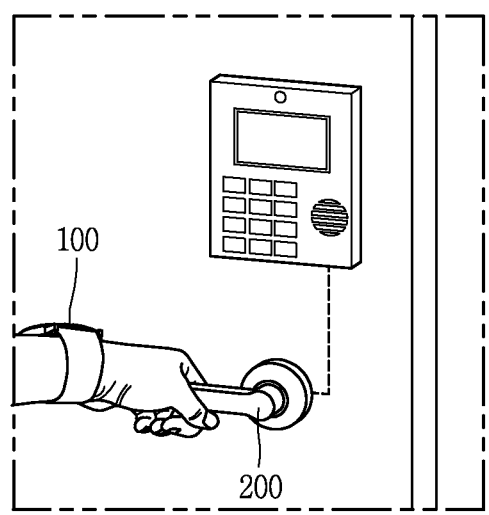
Figure 4C:
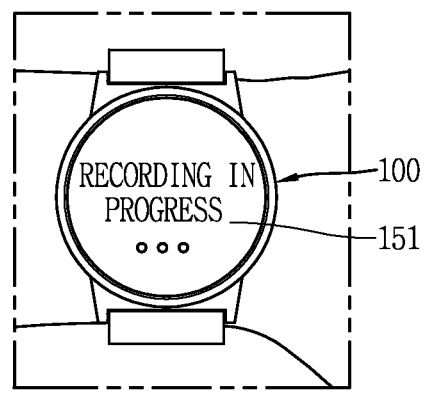

First, when it is sensed, as illustrated in FIG. 4A, that the watch-type mobile terminal 100 is worn on the wrist of the user, the mobile terminal 100 records the movement information on the wearer and the biological signal of the wearer while the wearer of the main body 301, as illustrated in FIG. 4B, performs a gesture of turning a door knob 200 to open the door (the recording mode). Then, the mobile terminal 100 stores the movement pattern of the wearer corresponding to the movement information on the wearer and the biological signal of the wearer in a "situation of turning the door knob 200 to open the door." When the movement pattern corresponding to the specific situation is stored in this manner, even though a third party wears the mobile terminal 100 and then performs a movement in the same movement pattern, there is no need for a separate authentication for security because a value of the biological signal that is sensed is different. On the other hand, while the recording mode is activated in this manner, as illustrated in FIG. 4C, graphic objects that indicate that the recording of the movement information on the wearer and the biological signal of the wearer is in progress, for example, a text "recording in progress," and a dot image " . . . " indicating that the recording is in progress are output to the display unit 151.

Figure 4D:
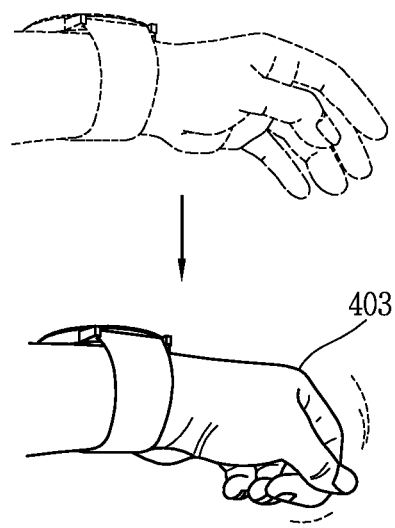
Figure 4E:
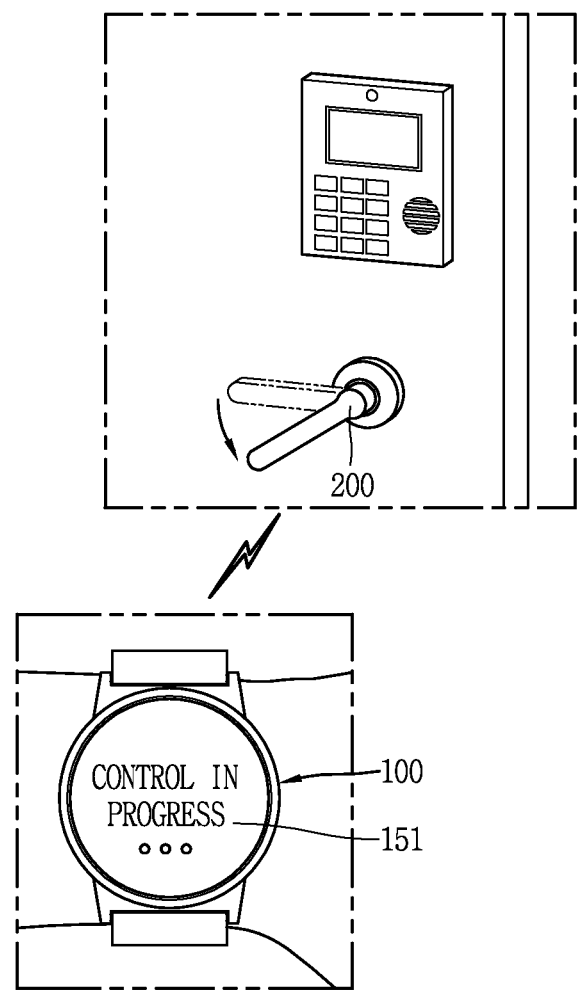

The movement pattern of the wearer corresponding to the "situation of turning the door knob to open the door" is stored in this manner, when an already-stored gesture 403 of turning the door knob 200 to open the door, which corresponds to the specific situation, is performed as illustrated in FIG. 4D, the mobile terminal 100 performs comparison to determine whether the gesture 403 is matched with the already-stored movement pattern. When as a result of the comparison, the gesture 403 is matched with the movement pattern corresponding to the "situation of turning the door knob 200 to open the door," which is stored in FIG. 4B, the wirelessly-connected door knob 200 is turned to open the door as illustrated in FIG. 4E, and graphic objects that indicate that the controlling of the external device is in progress, for example, the text "control in progress" and the dot image " . . . " indicating that the controlling is in progress are output to the display unit 151 of the mobile terminal 100.

On the other hand, although not illustrated, when the wearer of the mobile terminal 100 performs a gesture of actually turning the door knob 200 to open the door, subsequent to the movement illustrated in FIG. 4E, the update to the newly-recorded movement information and biological signal are performed. Accordingly, even when the habitual gesture of the wearer is changed, the external device is controlled with the changed habitual gesture without needing to store the new movement pattern.

As described above, according to the embodiment of the present disclosure, the movement of the wearer and the pattern of the biological signal of the wearer that are recorded in a specific situation are stored, and when the movement and biological signal that are the same as the stored pattern are sensed thereafter, the external device associated with the specific situation is possible to control. Accordingly, even in a situation where the wearer has difficulty in directly controlling the external or in performing inputting on the worn mobile terminal, the external device can be controlled only with the recorded habitual gesture.

A method of displaying the screen information associated with the gesture of wearer in the recording mode or the control mode is described below referring to FIGS. 6A to 6F and 8A to 8E.

First, the sensing unit 140 of the mobile terminal 100 senses the wearing of the main body. When the wearing of the main body is sensed, the mobile terminal 100 outputs a signal or information corresponding to the wearing of the main body. In addition, based on the biological signal of the wearer that is sensed according to the wearing of the main body 301, the user authentication is performed on the wearer in a natural manner.

After the wearing of the main body 301 is sensed in this manner, the controller 180 activates either of the recording mode and the control mode. To do this, when the first input signal is input in a specific situation through the user input unit 123 and then the movement information on the wearer of the main body and the biological signal of the wearer are sensed, the controller 180 recognizes that the control command for activating the recording mode is input. In addition, when the movement information on the wearer of the main body 301 and the biological signal of the wearer is sensed directly through the user input unit 123, the controller 180 recognizes this as the input of the control command for activating the control mode.

When in this manner, the mobile terminal is worn and then the input of the control command corresponding to the activation of the recording mode or the control mode is sensed through the user input unit 123, the screen information corresponding to a specific situation is output to the display unit 151 of the mobile terminal 100 while the recording mode is activated or while the control mode is activated.

Figure 6A:
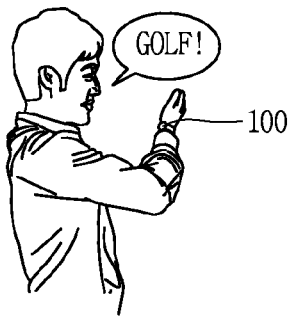
FIGS. 6A to 6D are diagrams for describing a method of recognizing the gesture of the wearer of the mobile terminal and displaying screen information associated with the gesture, according to the embodiment of the present disclosure.
Figure 6B:

For example, when the wearer of the mobile terminal 100 inputs a voice "golf" into the mobile terminal 100 as illustrated in FIG. 6A, the mobile terminal 100 activates the recording mode for "golf" that is defined as a specific situation, and while the recording mode is activated, outputs to the display unit 151 already-stored content associated with gold motion, for example, an image (or a moving image) 601 of a golf swing gesture as illustrated in FIG. 6B. On the other hand, although not illustrated, based on muscles, shapes of tendons, and a change in grip strength that are sensed through the camera 121 and/or the sensing unit 140 that are provided in the main body 301, the mobile terminal 100 can recognize "gold" as a specific situation.

In addition, in the recording mode or the control mode, the controller 180 recognizes a gesture corresponding to the movement information on the wearer and the biological signal of the wearer, conducts a web search for at least one image associated with the recognized gesture and provides the searched-for image to display unit 151. In addition, the controller 180 transfers the searched-for image to the external device through the wireless communication unit 110.

At this point, when the gesture corresponding to the movement information on the wearer and the biological signal of the wearer are changed, the controller 180 again conducts a web search for an image corresponding to the changed gesture and provides the searched-for image to the display unit 151. For example, if a wearer's posture is changed from a first gesture to a second gesture in the recording mode for "gold" that is a specific situation, based on the biological signal (including meta data associated with this posture change) that is sensed through the sensing unit 140, the controller 180 recognizes the gesture change and can conduct a web search for an image associated with the second gesture.

Figure 6C:
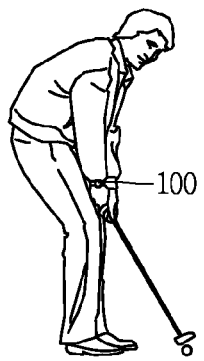
Figure 6D:
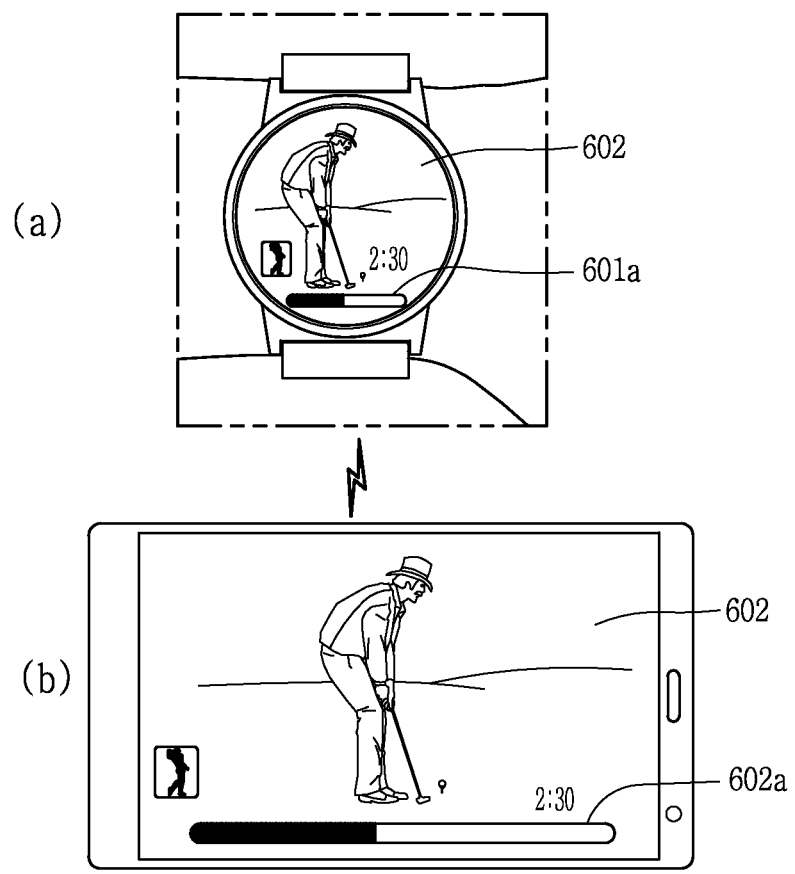

For example, as illustrated in FIG. 6C, according to the activation of the recording mode or the control mode, change values of the movement information and the biological signal are recorded while the wearer of the main body 301 performs a swing gesture in "golf" that is defined as a specific situation. In addition, as illustrated in FIG. 6D, the mobile terminal 100 conducts a web search for an image that is suitable for the gesture of the wearer that changes while the recording mode or the control mode is activated and outputs the searched-for image to display unit 151 (*a*) or provided it to the external device 200 (*b*).

In addition, in the recording mode or the control mode, the controller 180 outputs to the display unit 151 the screen information that includes a first graphic object indicating the activation of the recording mode or the control mode and a second object indicating the extent to which the movement information on the wearer and the biological signal of the wearer are changed.

In addition, in the recording mode or the control mode, the controller 180 may further include a third graphic object indicating time information corresponding to the activation of the recording mode or the control mode and a fourth graphic object indicating the extent to which the movement information on the wearer and the biological signal of the wearer are matched to the already-stored movement pattern.

At this point, the already-stored movement pattern, as described above, may be the movement information on the wearer and the biological signal of the wearer that are recorded in the recording mode or may be a target value or right posture information that is set through the user input.

For example, referring back to FIG. 6D, indicator icons 601*a* and 602*a* that indicate a moving speed of the wearer, grip strength of the wearer, an extent of change in wearer's strength thrown into his/her fingers, and time information that are sensed through the sensing unit 140 of the mobile terminal 100 are further displayed on the screen information that is output to the display unit 151 or to a screen of the external device 200.

In this manner, in the recording mode, the control mode, and a normal mode, the different pieces of screen information are displayed on the display unit 151 of the mobile terminal 100 according to the embodiment of the present disclosure.

Figure 8A:
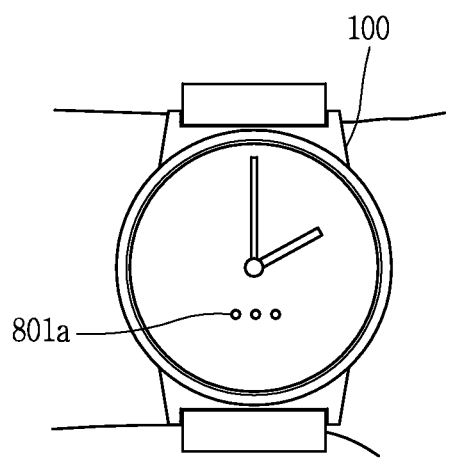
FIGS. 8A to 8E are diagrams for describing a method of displaying the screen information associated with the gesture of the wearer in a recording mode or a control mode in the mobile terminal, according to the embodiment of the present disclosure.

Specifically, in the normal mode, the mobile terminal 100 senses only basic state information on the wearer of the main body 301 through the sensing unit 140. For example, the mobile terminal 100 senses whether or not the wearer is in the sleep state or in the awakened state and whether or not the wearer's strength thrown in a body portion on which the main body 301 is worn is changed. As a result, as illustrated in FIG. 8A, in the normal mode, along with information indicating time, an image (for example, a dot image) indicating that the sensing of the biological signal is in progress is output to the center of the display unit 180 of the mobile terminal 100 according to characteristics of the watch-type mobile terminal 100.

In addition, in the recording mode, the mobile terminal 100 records all pieces of movement information and all biological signals that are sensed in a specific situation. For example, the mobile terminal 100 senses the moving speed of the wearer, the grip strength of the wearer, the gesture according to the change in the wearer's strength thrown into his/her fingers, or the posture change through the sensing unit 140.

Figure 8B:
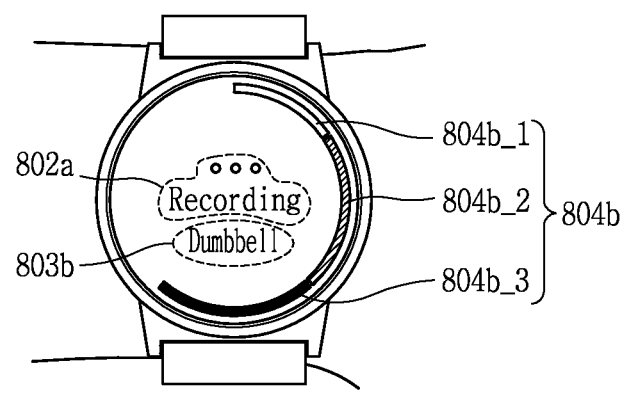
Figure 8C:
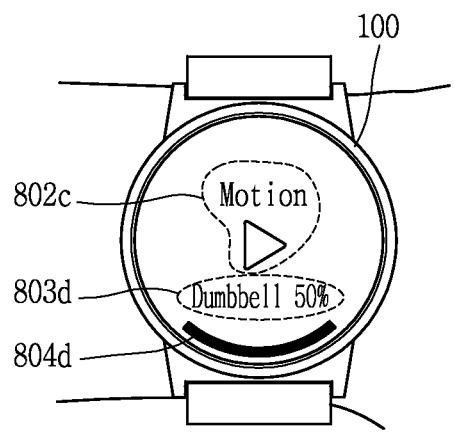

As a result, as illustrated in FIG. 8B, a first image 802*a* indicating that the activation of the recording mode is in progress, a second image (for example, an image of a dumbbell) 803*b* indicating a specific condition associated with the recording mode, and a third image 804*b* indicating the time information that corresponds to the activation of the recording mode and an amount of the movement (for example, the moving speed, the grip strength, or the extent of the strength change) are output to one region of the display unit 151. At this point, the third image 804*b* is displayed in such a manner that sections that are the same in the amount of the movement are visually distinguished (displayed in different colors) from one another. That is, the third image 804*b* are divided by the movement of the wearer into a first section 804*b*_1, a second section 804*b*_2, and a third section 804*b*_3, and the length of each section is displayed in such a manner that it is in proportion to the time for which the movement continues.

Figure 8D:
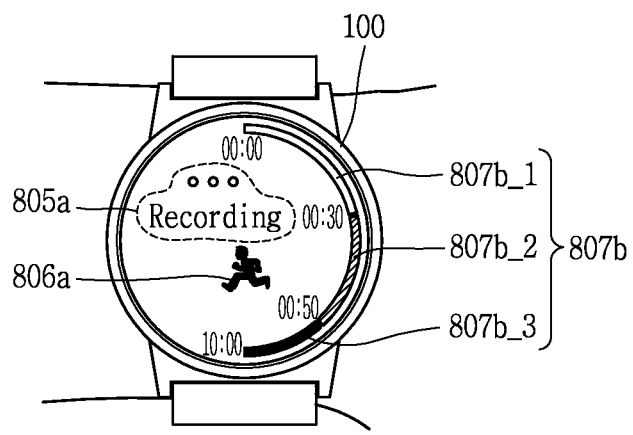

In addition, as illustrated in FIG. 8D, in the recording mode, a first image 805*a* indicating that the recording mode is in progress, a web search image (for example, an image of a running person) 806*a* corresponding to a gesture of the wearer that is recognized while the recording mode is activated, and a third image 807*b* indicating the extent to which the movement information on the wearer and the biological signal of wearer are matched with the already-stored movement pattern are output to one region of the display unit 151. At this point, the already-stored movement pattern is either predetermined target value or recommended-posture information. Accordingly, the third image 807*b* is displayed in such a manner that sections that are the same in the extent to which the sensed movement information and biological signal are matched with the already-stored movement pattern are visually distinguished from one another. For example, the larger the extent to which the sensed movement information and biological signal are matched with the already-stored movement pattern, the deeper is colors of displayed sections 807*b*_1, 807*b*_2, and 807*b*_3 of the third image 807*b*.

In addition, in the control mode, the mobile terminal 100 generates a control command corresponding to the already-stored movement pattern in the situation that corresponds to the movement information on the wearer and the biological signal of the wearer that are sensed through the sensing unit 140. The generated control command controls performing of a specific function of the mobile terminal 100 and/or controls operation of the connected external device.

Figure 8E:
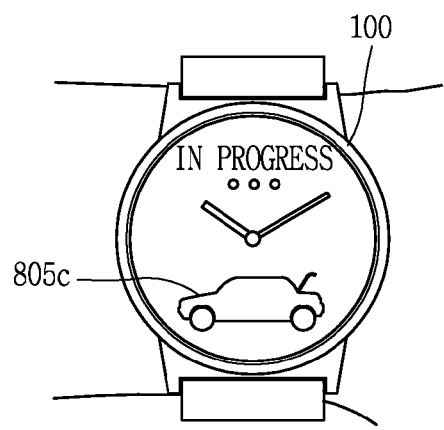

As a result, as illustrated in FIGS. 8B and 8E, an image associated with a specific situation corresponding to the movement information on the wearer and the biological signal of the wearer that are sensed is displayed, in the form of a text image 803*d*, on one region of the display unit 151, or is displayed, in the form of a dynamic image 805*c* indicating a device or a function that is controlled by the control command, on one region of the display unit 151. In addition, in the control mode, in addition to that, an image 802*c* indicating that the activation of the control mode is in progress, and an image 804*d* indicating the time for which the activation of the control mode continues are further displayed on the display unit 151.

As described above, according to the embodiment of the present disclosure, in the recording mode and the control mode, the pieces of information associated with the movement information on the wearer who wears the mobile terminal 100 and the biological signal of the wearer are displayed on the display unit 151, and thus although a specific function is controlled only with the habitual gesture, the wearer can recognize this in an easy manner.

A method of sensing the movement pattern of the wearer and thus controlling the external device that is connected to the mobile terminal is described in detail below referring to FIGS. 7A to 7D.

When the user authentication is performed on the wearer according to the wearing of the main body 301, through the wireless communication unit 110, the controller 180 senses that the mobile terminal 100 is connected to the external device. When the connection to the external device is sensed, the controller 180 generates a control command for activating either the recording mode or the control mode associated with the connected external device and provides the generated control command to the user input unit 123. At this point, selection of either the recording mode or the control mode is determined based on a current operation state of the connected external device. For example, when the current operation state of the external device is a setting mode in which specific information is received from the mobile terminal 100, the mobile terminal 100 make a determination in such a manner that the recording mode is activated.

When the recording mode associated with the connected external is activated, the movement information on the wearer and the biological signal of the wearer are recorded. At this point, the recorded movement information on the wearer and the recorded biological signal are provided to the connected external device every predetermined time or real time according to setting of the mobile terminal or the connected external device.

When the control mode associated with the connected external device is activated, the already-stored movement pattern in a specified situation that corresponds to the movement information on the wearer and the biological signal of the wearer is detected, and the corresponding control command is generated. The mobile terminal 100 transfer the generated control command to the connected external device and controls specific operation of the electronic apparatus.

On the other hand, if the multiple external devices are connected to the main body 301, based on information on the time for which the connected external devices are used and information on ambient sound, the controller 180 can select one external device that is suitable for activating the control mode.

Figure 7A:
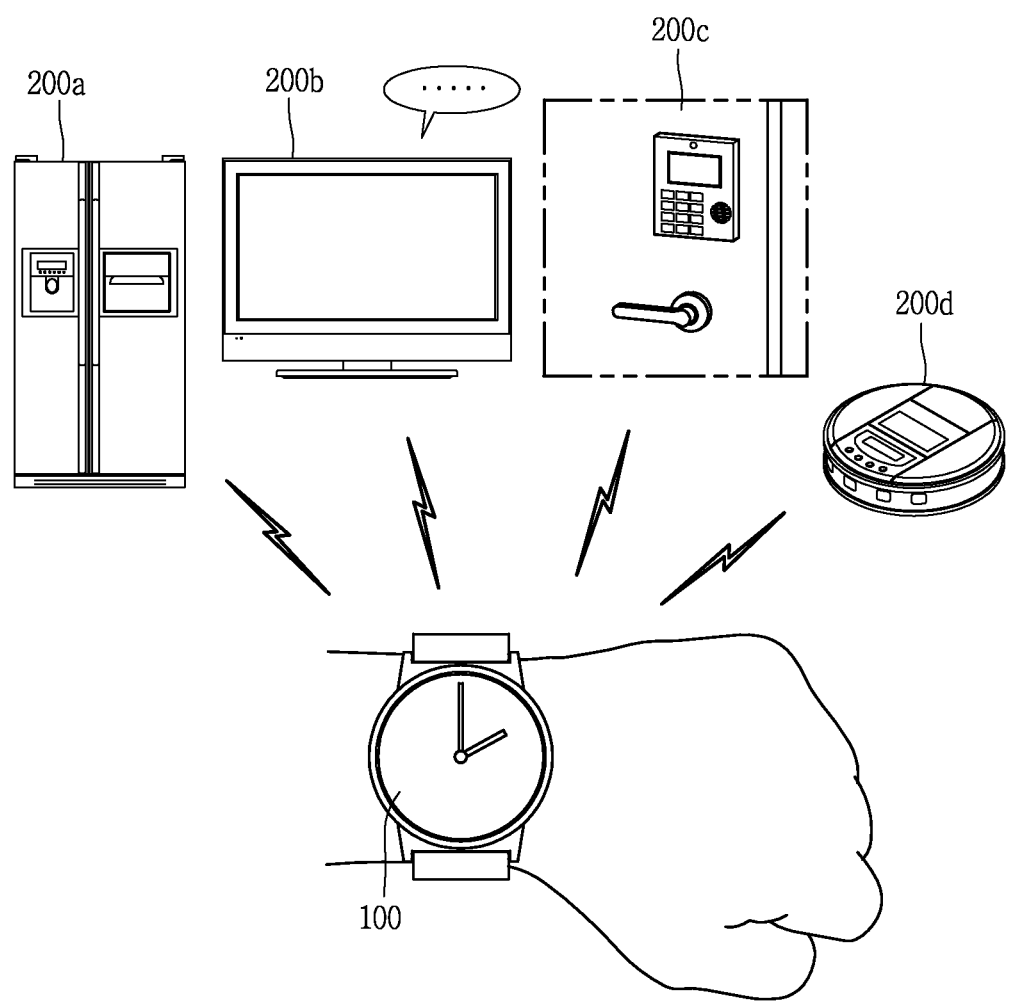
FIGS. 7A to 7D are diagrams for describing a method of detecting a pattern of a movement of the wearer and controlling an external device connected to the mobile terminal, according to according to the embodiment of the present disclosure.
Figure 7B:
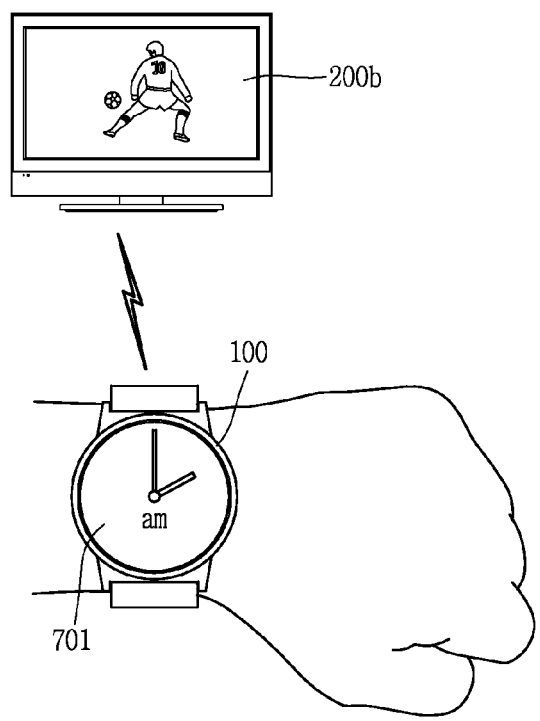
Figure 7C:
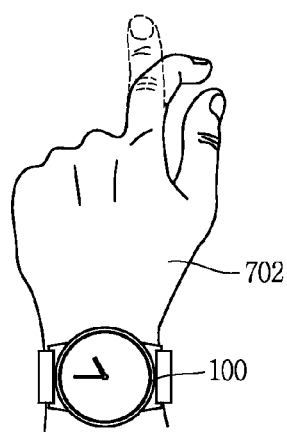
Figure 7D:
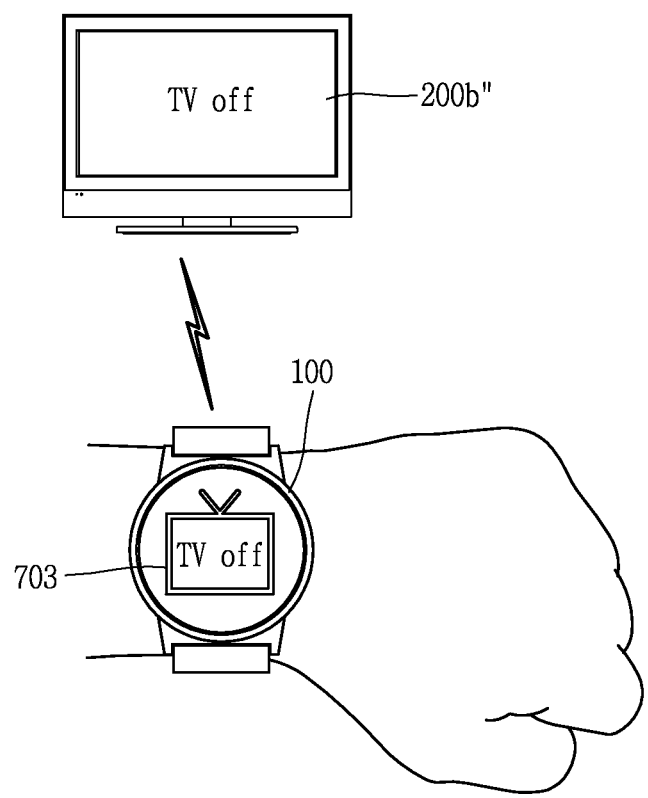

For example, if the watch-type mobile terminal 100, as illustrated in FIG. 7A, are wirelessly connected to multiple external devices, for example, a refrigerator 200*a*, a smart TV 200*b*, a door 200*c*, and a cleaner, based on current time information and a level of a sound volume that is transferred from the smart TV 200*b*, the mobile terminal 100, as illustrated in FIG. 7B, selects the smart TV 100*b* as the external device that is suitable for activating the control mode. When after selecting the external device, as illustrated in FIG. 7C, the wearer performs a hand gesture 702 (for example, a gesture in which a forefinger is bent and the other fingers are curled in towards the palm) that is the same as an already-stored "TV power off" movement pattern, the smart TV 200*b*, as illustrated in FIG. 7D, is powered-off (200*b*"), and a thumbnail image and an operation state of the smart TV 200*b* are displayed, as a dynamic image 703, on the display unit 151 of the mobile terminal 100.

In addition, although not illustrated, if the multiple external devices are connected to the main body 301, a thumbnail image of each of the multiple connected external devices is displayed on the display unit 151, and the control mode can be activated with respect to the external device corresponding to one selected from the multiple thumbnail images.

FIGS. 9A to 9F are diagrams for describing a method of recognizing repetition of the movement pattern of the wearer and displaying information associated with this, according to the embodiment of the present disclosure.

In the recording mode, the controller 180 recognizes the repetition of the movement pattern that occurs in a specific situation. That is, the controller 180 accumulates and records the movement pattern of the wearer that is generated initially and the movement patterns of the wearer that are subsequently generated in the same situation, in chronological order.

When the repetition of the movement pattern occurring in a specific situation is recognized, the controller 180 further stores accumulation information on and average information on the repeated movement patterns.

Then, in the recording mode or the control mode, the controller 180 displays to one region of the display unit 151 additional information associated with the accumulation information and the average information on the repeated movement patterns of the wearer.

In addition, when a second input signal is sensed in the specific situation, the controller 180 provides information corresponding to the movement information on the wearer and the biological signal of the wearer that are repeatedly stored in the recording mode, to the connected external device. At this point, the second input signal is a predetermined voice command, a gesture, a key operation, or a transmission signal that is automatically generated every predetermined time (for example, 9:00 A.M).

Figure 9A:
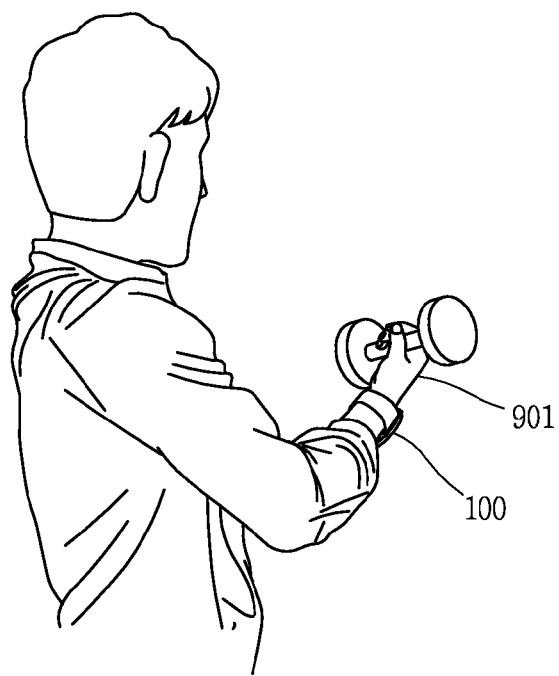
FIGS. 9A to 9F are diagrams for describing a method of recognizing repetition of the pattern of the movement of the wearer and displaying associated information, according to the embodiment of the present disclosure.
Figure 9B:
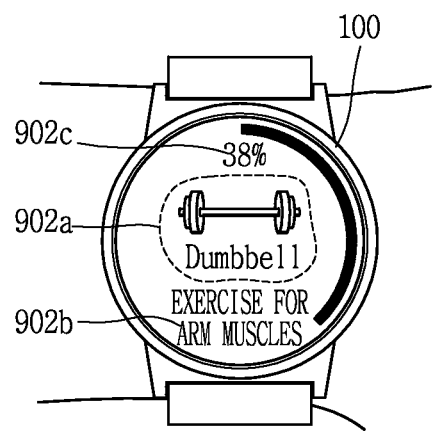

For example, if illustrated in FIG. 9A, the wearer performs a gesture 901 of actually lifting up a dumbbell while wearing the mobile terminal 100, the mobile terminal 100 senses the movement information on the wearer and the biological signal of the wearer and recognizes whether or not the same gesture as the gesture of lifting up the dumbbell is repeated. While the gesture of lifting up the dumbbell is performed, as illustrated in FIG. 9B, pieces of additional information, such as an image 902a corresponding to the recognized gesture 901, position information 902b on the used tendons or muscles, and information 902c on a current amount of exercise against a target amount of exercise, are displayed in the display unit 151 of the mobile terminal 100.

Figure 9C:
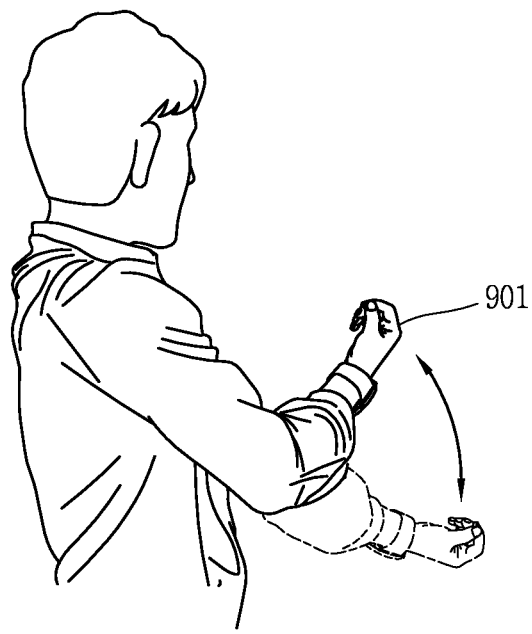
Figure 9D:
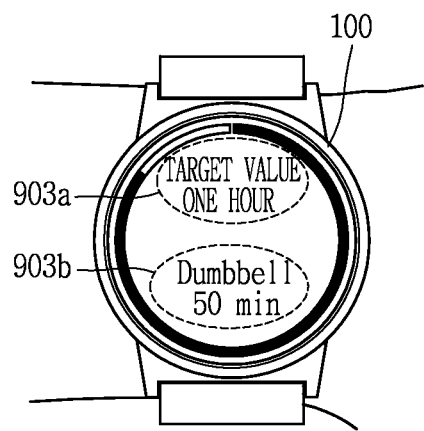

Subsequently, if the wearer of the main body 301 performs the gesture 901 without the dumbbell as illustrated in FIG. 9C, based on the accumulation information and the average information on the repeated movement pattern of the wearer, information 903a on a target value to accomplish for a predetermined time period (for example, one day) and information 903b on an amount of exercise accomplished against a target value for the predetermined time period are displayed on the display unit 151 as illustrated in FIG. 9D. In addition, although not illustrated, based on the movement patterns that are repeated and accumulated for a predetermined time period, the mobile terminal 100 automatically changes the predetermined target value.

Figure 9E:
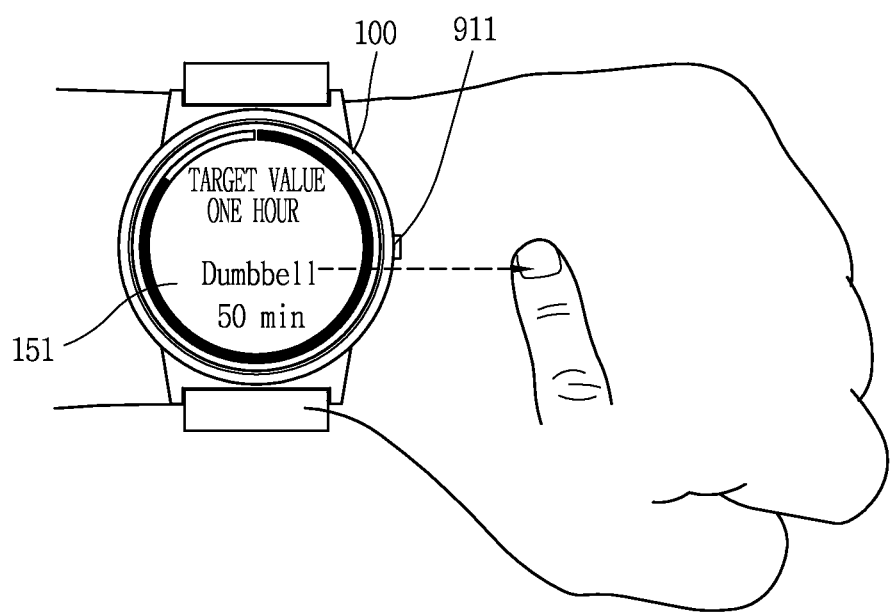
Figure 9F:
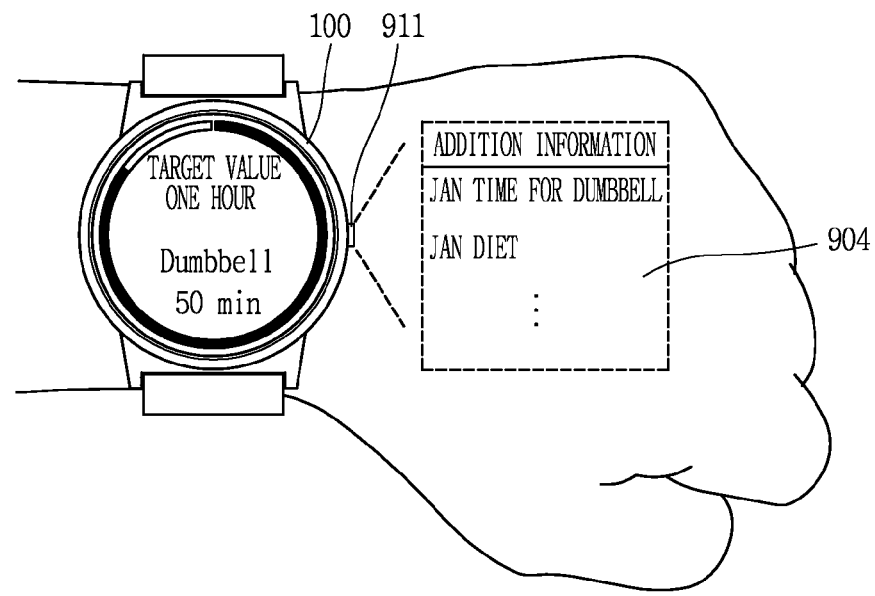

In addition, based on information on an amount of exercise against the target value, the mobile terminal 100 provides information associated with a proper diet and how to take exercise to the user. On the other hand, if the size of the display unit 151 is small like that of the watch-type mobile terminal 100, such pieces of information are difficult to provide. To solve such a problem, the mobile terminal 100 according to the embodiment of the present disclosure, as illustrated in FIGS. 9E and 9F, includes a projection unit 911 that projects image information using light, in one region of the main body 301, for example, on a lateral surface thereof. Thus, when the wearer performs drag touch inputting on the display unit 151 in a predetermined direction (for example, in a direction of a wrist (FIG. 9E), the mobile terminal 100 projects additional information 904 associated with the proper diet, how to take exercise, or the like onto one portion of the back of the hand as illustrated in FIG. 9F.

Figure 10A:
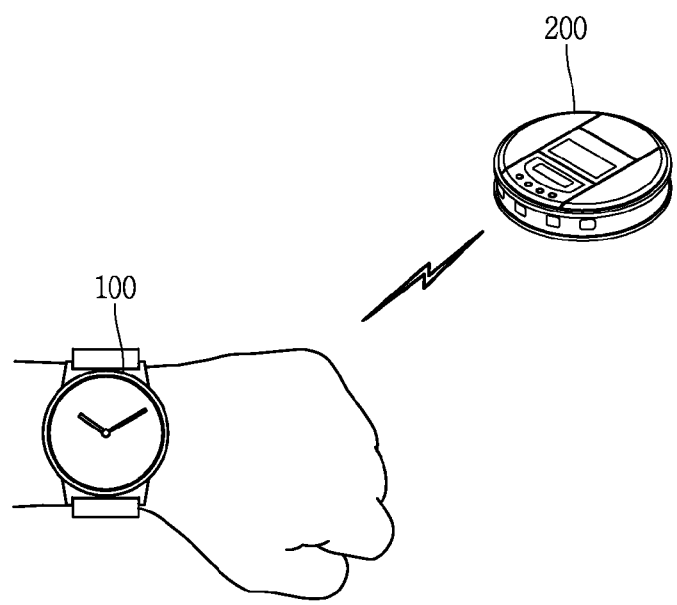
FIGS. 10A to 10D are diagrams for describing a method of controlling the external device using position information corresponding to changes in the movement information on the wearer and the biological signal of the wearer, according to the embodiment of the present disclosure.
Figure 10B:
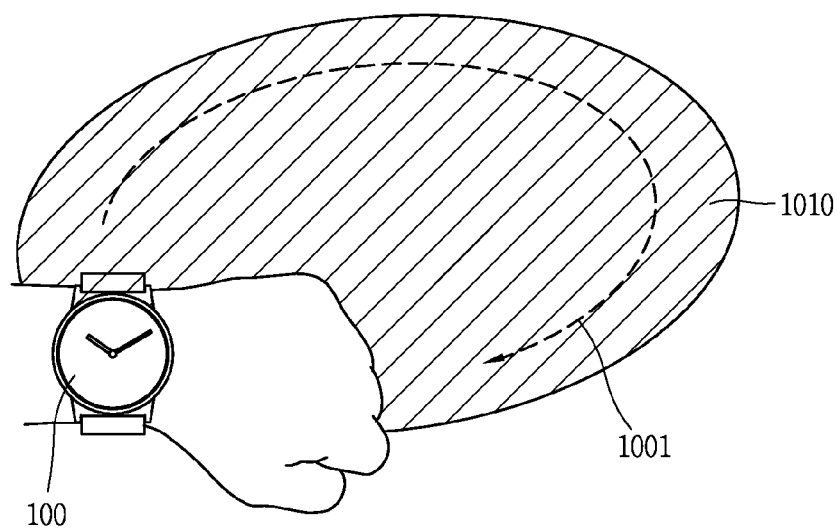
Figure 10C:
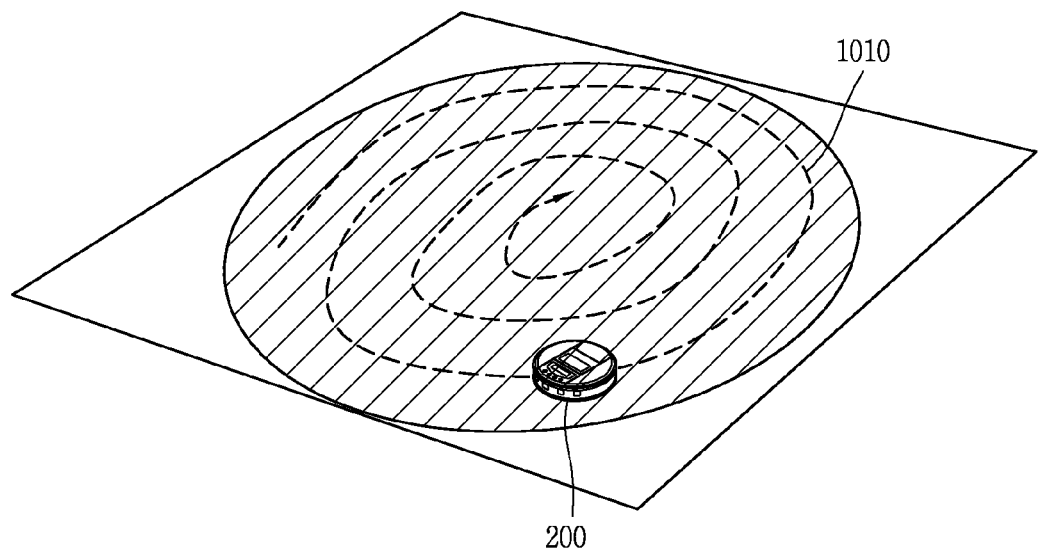
Figure 10D:
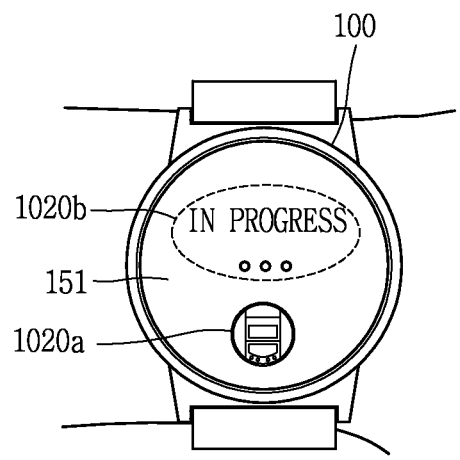

On the other hand, FIGS. 10A and 10D illustrate a method of controlling the external device using the position information corresponding to changes in the movement information on the wearer and the biological signal of wearer, according to the embodiment of the present disclosure.

To do this, the watch-type mobile terminal 100 according to the embodiment of the present disclosure includes the wireless communication unit 110 for receiving the position information on the main body 301. Then, when the control mode is activated, the controller 180 receives the position information corresponding to the changes in the movement information on the wearer and the biological signal of the wearer in a specific situation and provided the received position information to the connected external device. For example, the mobile terminal 100 senses the movement information on the wearer and the biological signal of the wearer that correspond to the first gesture and thus recognizes that the position information starts to be received. In addition, the mobile terminal 100 may receive the position information that changes according to the wearer's movement and at the same time, may drive the camera 122 provided in the main body 301 in order to grasp the exact position information. In addition, the mobile terminal 100 senses the movement information on the wearer and the biological signal of the wearer that correspond to the second gesture and thus recognizes that the receiving of the position information is finished. When the position information corresponding to the movement information on the wearer and the biological signal of the wearer is provided to the external device, the external device utilizes the received position information in performing the operation thereof.

For example, when the watch-type mobile terminal 100 and the external device, for example, a robot cleaner 200, are wirelessly connected to each other as illustrated in FIG. 10A, the wearer can set a specific area that the robot cleaner 200 has to clean up, using the mobile terminal 100. That is, as illustrated in FIG. 10B, when the wearer performs a gesture (a hand gesture in which the fingers are curled in toward the palm and are spread out) corresponding to a designated starting point on a cleaning-target area that the robot cleaner 200 has to clean up, then moves along a border 1001 of the cleaning-target area, and then performs a gesture (a hand gesture in which the fingers are spread out and are curled in toward the palm) corresponding to a designated ending point on the cleaning-target area, an area 1010 to clean up is defined by the border along which the wearer moves. Then, the cleaner 200 performs cleaning operation on the area 1010 to clean up through the mobile terminal 100 as illustrated in FIG. 10C, a thumbnail image 1020a of the cleaner 200 and an image 1020b indicating that the cleaning operation is performed are displayed on the display unit 151 of the mobile terminal 100 as illustrated in FIG. 10D.

At this point, the position information corresponding to the movement of the wearer is transferred to the cleaner 200 along with the time information, and thus the mobile terminal can transfer associated information to the cleaner 200 in order for the cleaner 200 to clean up an area more clearly where the wearer stays for more than a reference time.

FIGS. 11A to 11D are diagrams for describing a method of displaying to the mobile terminal the screen information associated with a feedback signal that is provided by the connected external device, according to the embodiment of the present disclosure.

When the wearing of the main body 301 is sensed and then a wearer's gesture for activating the control mode is recognized, the controller 180 transfers a control command associated with the recognized gesture to the connected external device. At this point, because the wearer's gesture corresponds to the wearer's habitual gesture that occurs in a specific situation, normally, a malfunction may occur in the external device when the wearer performs the habitual gesture in error. To solve such a problem, when the wearer's habitual gesture occurs, the mobile terminal 100 according to the embodiment of the present disclosure may additionally perform processing that transmits and receives the feedback signal to and from the associated external device.

Specifically, when a first signal responding to the receiving of the control command corresponding to the movement pattern from the connected external device is received, the controller 180 outputs to the display unit 151 first screen information corresponding to the first signal.

Then, when a second signal corresponding to a result of performing the control command is received from the connected external device according to the input of a signal for checking the first information, the controller 180 outputs to the display unit 151 second screen information corresponding to the second signal. At this point, the input of the signal for checking the first screen information is one among a predetermined voice command, a gesture, or touch input applied to the display unit 151 or a specific key.

Figure 11A:
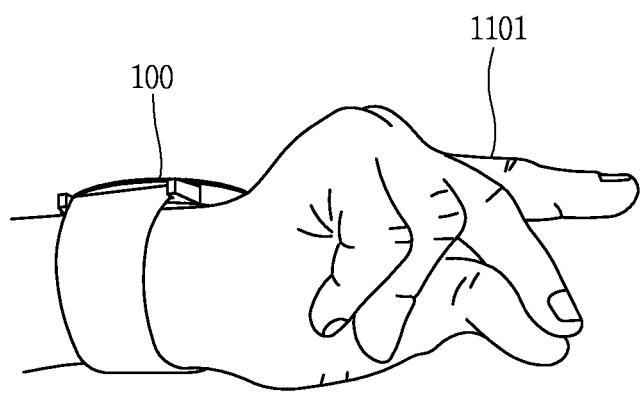
FIGS. 11A to 11D are diagrams for describing a method of displaying the screen information associated with a feedback signal that is provided by the connected external device, according to the embodiment of the present disclosure.
Figure 11B:
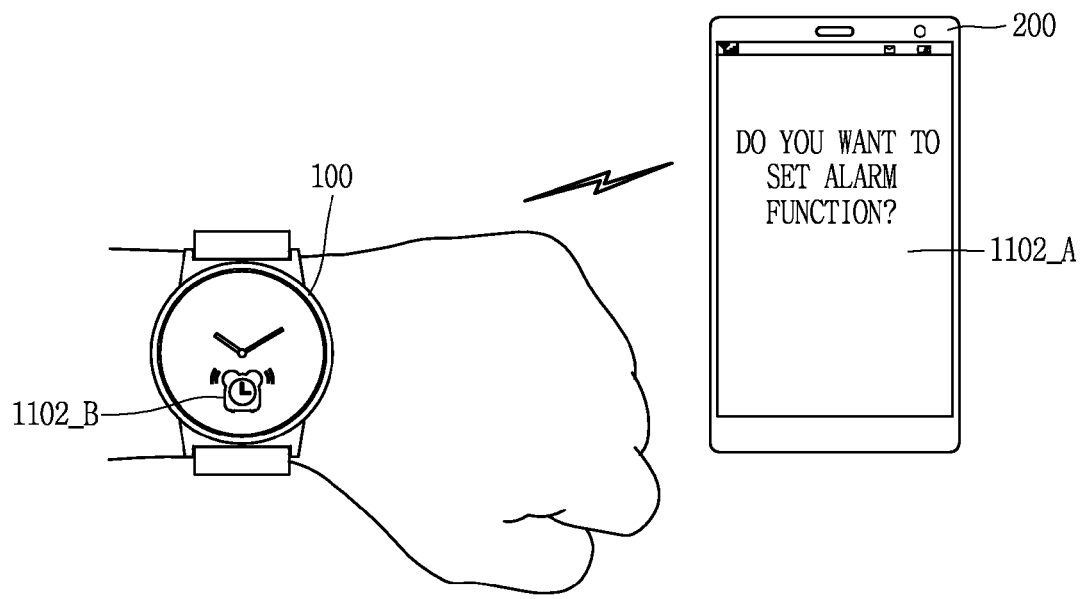
Figure 11C:
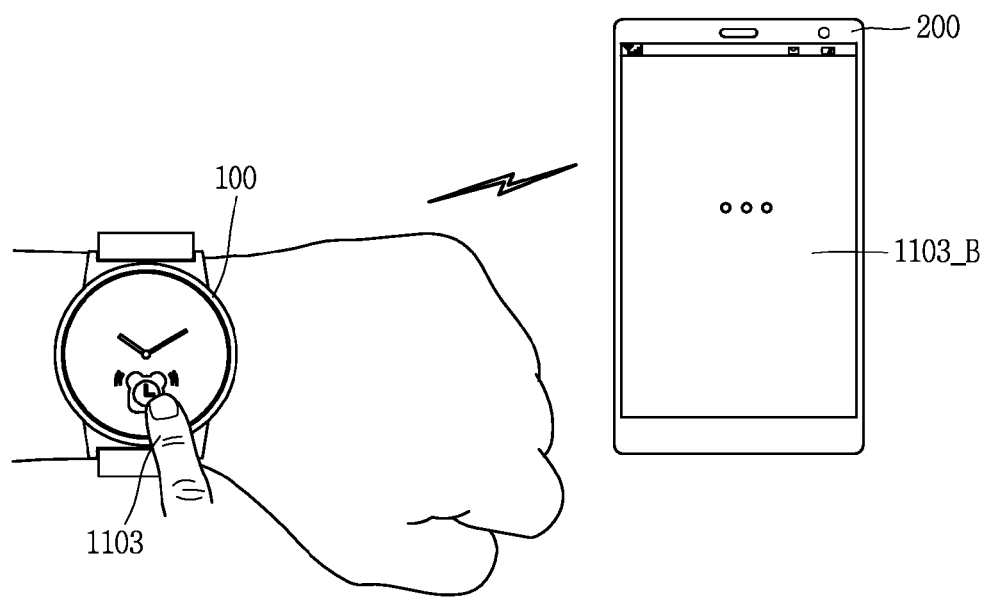
Figure 11D:
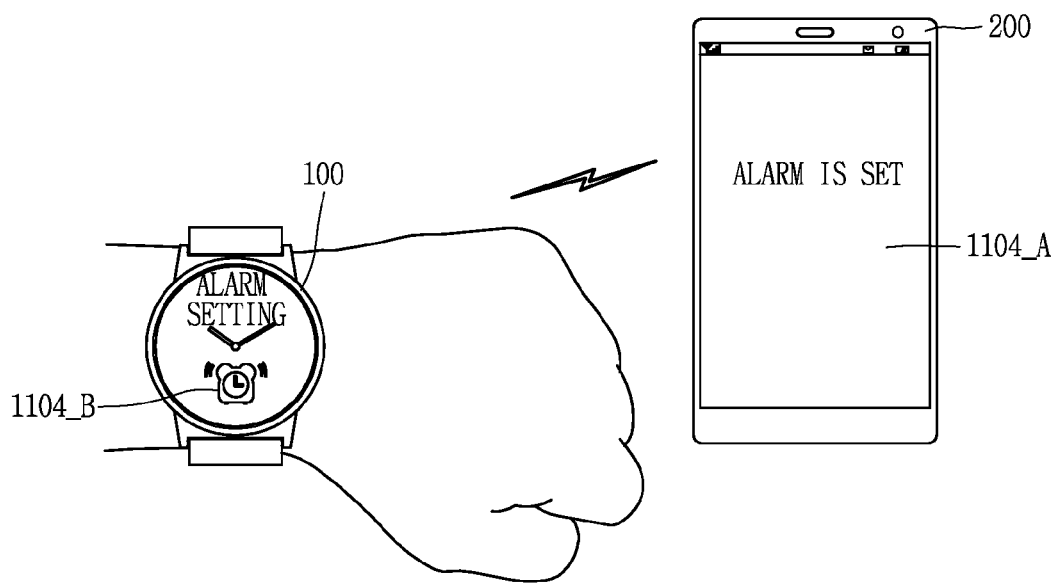

For example, referring to FIG. 11A, when the wearer of the mobile terminal 100 performs a specific gesture, for example, a hand gesture 1101 of connecting a thumb and a middle finger and throwing strength into them in the opposite direction, the mobile terminal 100 senses the movement information on the wearer and the biological signal of the wearer and recognizes the hand gesture 1101 without driving the camera 122. For example, when the corresponding hand gesture 1101 is a habitual gesture corresponding to an "alarm function," the mobile terminal generates a control command for performing control in such a manner that the "alarm function" is turned on, and transferred the control command the connected external device 200. Before performing the "alarm function," the external device 200 that receives the generated control command, as illustrated in FIG. 11B, outputs a message 1102_A asking whether or not the alarm function is set, and a signal (the "first signal" described above) corresponding to the corresponding message 1102_A is received in the mobile terminal 100. Then, an image 1102_B indicating whether or not the "alarm function" is set is displayed on the display unit 151 of the mobile terminal 100. When the wearer performs touch input on the displayed image 1102_B as illustrated in FIG. 11C, the mobile terminal 100 recognizes this as inputting a signal that checks the displayed image 1102_B and provides the signal to the connected external device 200 (1103_B). Then, the "alarm function" is set in the connected external device 200 as illustrated in FIG. 11D, and a message 1104A "Alarm is set" is output to the screen. Then, the setting of the "alarm function" in the connected external device 200 is finished, an image 1104_B indicating that the "alarm function is set" is displayed on the display unit 151 of the mobile terminal 100.

According to the embodiments described above, the wearer of the mobile terminal controls a specific function of the mobile terminal or the connected external device only with the habitual gesture. A method of performing a specific function of the external device when the wearer cannot perform even the habitual gesture is described below.

Figure 12A:
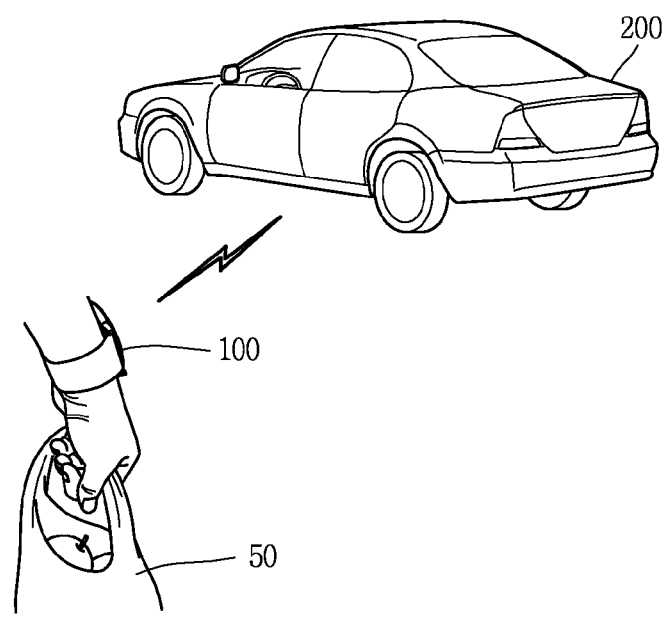
FIGS. 12A to 12C are diagrams illustrating a method of controlling the external device in a different manner based on state information on the wearer, according to the embodiment of the present disclosure.
Figure 12B:
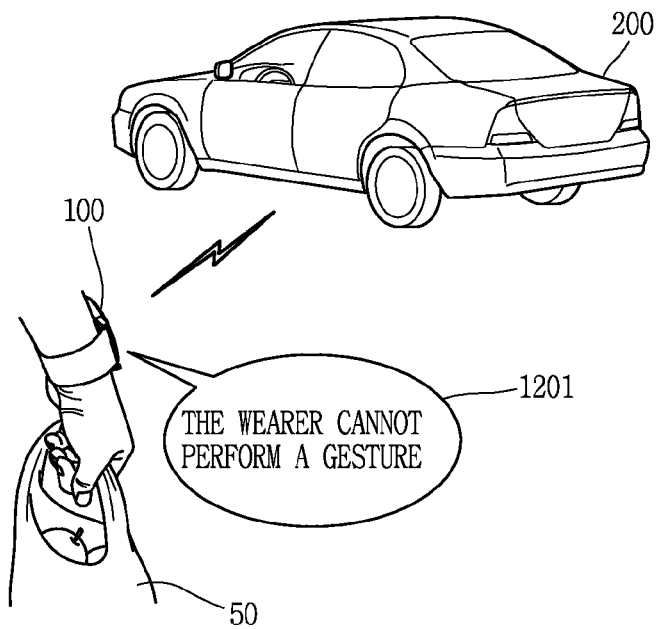
Figure 12C:
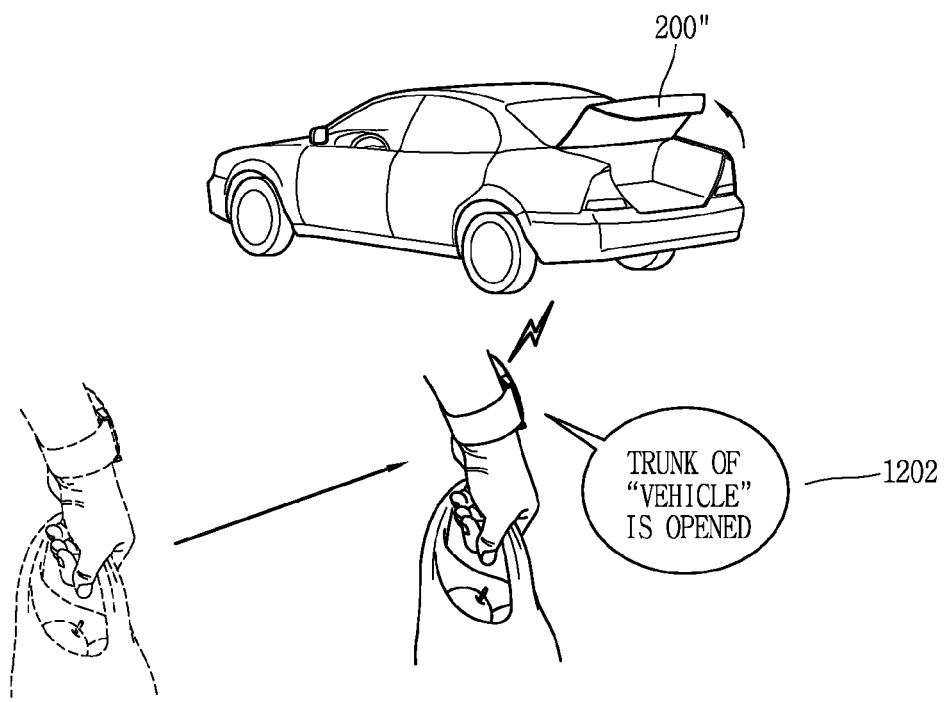

In association with this, FIGS. 12A to 12C are diagrams illustrating a method of controlling the external device in a different manner based on the state information on the wearer, according to an embodiment of the present disclosure.

When the mobile terminal 100 according to the embodiment of the present disclosure and the external device are connected with each other, the controller 180 provides to the connected external device the state information on the wearer that corresponds to the biological signal of the wearer. The state of the wearer may be determined by the mobile terminal 100 and may be determined by the external device that receives the biological signal of the wearer as is.

When it is determined that the state of the wearer is a state where the movement information for performing a specific function cannot be input, the controller 180 performs control in such a manner that the external device operates according to a control command that is input in a different input manner. At this point, the different input manner in which the control command is input includes a voice command and a different gesture (for example, a foot gesture) that can be recognized through the camera 133. In another example, a control command for performing a specific function is generated only with progressive proximity to the external device.

For example, as illustrated in FIG. 12A, assume that the wearer of the mobile terminal 100 wants to open a trunk of a vehicle that is wirelessly connected to the mobile terminal 100, but cannot perform a habitual gesture because he/she carries a thing 50 with his/her hand. Then, as illustrated in FIG. 12B, the mobile terminal 100 senses the biological signal of the wearer and thus recognizes a situation where the wearer carries the thing. Then, the mobile terminal 100 outputs a message "The wearer cannot perform a gesture" to the display unit 151 or the audio output module 152. At this point, this state of the wearer is possible to recognize also in a vehicle 200 that is wirelessly connected to the mobile terminal 100 and receives the biological signal of the wearer. Then, as illustrated in FIG. 12C, the mobile terminal 100 can open the trunk of the vehicle 200 only by the wearer moving toward the trunk of the vehicle 200 without performing the habitual gesture (200"). On the other hand, a message "The trunk of the vehicle is opened" that alerts the user to the control operation is output to the display unit of the mobile terminal 100 or the audio output module 152.

On the other hand, although not illustrating in the accompanying drawings or not specifically described above, the mobile terminal according to the embodiment of the present recognizes ambient intensity of illumination, ambient temperature, and ambient humidity, tries to establish a connection to an associated home appliance and performs a recorded habitual gesture. Thus, operation of the connected home appliance is possible to control.

In addition, the mobile terminal 100 senses the biological signal of the wearer and thus determined the state of the wearer (for example, an excited state and a sleep state) and accordingly controls the operation of the connected home appliance corresponding to the habitual gesture in a more specific manner. For example, if a habitual gesture for powering on an air-conditioner is performed, the mobile terminal 100 determines the state of the wearer and transfers not only a control command for powering on the air-conditioner, but also a control signal for controlling a setting temperature, a wind direction, or the like in the air-conditioner.

As described above, according to the embodiment of the present disclosure, the movement information on the wearer of the main body and the biological signal of the wearer is sensed in a specific situation and is recorded. Thereafter, when an occurrence of the same situation is recognized based on the recorded information and the sensing of the movement and biological signal of the wearer, a corresponding specific function is performed. Therefore, the wearer of the mobile terminal does not need to perform complex inputting in order to perform a specific function, and can perform a specific function only with a habitual gesture in a natural manner. In addition, the movement of the wearer and the pattern of the biological signal of the wearer that are recorded in a specific situation are stored, and when the same movement and biological signal as the stored pattern are sensed thereafter, the external device associated with the specific situation is possible to control. Accordingly, even in a situation where the wearer has difficulty in directly controlling the external or in performing inputting on the worn mobile terminal, the external device can be controlled only with the recorded habitual gesture.

In accordance with the purpose of this specification, as embodied and broadly described herein, there is provided a mobile terminal including: a main body; a sensing unit that senses wearing of the main body, movement information on a wearer, and a biological signal of the wearer; a user input unit into which a control command is input for activating either a recording mode or a control mode when the wearing of the main body is sensed; and a controller that, in the recording mode, records the movement information on the wearer and the biological signal of the wearer in a specific situation and stores a movement pattern that occurs in the specific situation and which, in the control mode, senses the movement information on the wearer and the biological signal of the wearer and when the already-stored movement pattern in the specific situation that corresponds to the movement information and the biological signal that are sensed is detected, provides a control command corresponding to the detected movement pattern to a connected external device.

In the mobile terminal, when a first input signal is input and then movement information and the biographic signal are sensed, the controller may generate a control command for activating the recording mode in a specific situation corresponding to the first input signal and may provide the generated control command to the user input unit, and when the first input signal is input and then the movement information on the wearer and the biological signal of the wearer that exceed a reference value is sensed, the controller may generate a control command for activating the control mode and may provide the control command to the user input unit.

In the mobile terminal, the first input signal may be a sensing signal that corresponds to a connection between the wearer of the main body and the external device.

In the mobile terminal, the specific situation may be recognized based on at least one among the first input signal, ambient image information that is obtained through a camera in the main body, and position information on the main body that is received through a wireless communication unit.

In the mobile terminal, when the connection between the main body and the external device is sensed, the controller may provide the control command for activating the recording mode or the control mode associated with the connected external device to the user input unit.

In the mobile terminal, if the multiple external devices are connected to the main body, a specific external device for activating the control mode may be selected based on pieces of time information on and pieces of ambient sound information on the connected external devices.

The mobile terminal may further include a display unit to which screen information corresponding to the specific situation in the recording mode, in which the screen information may include a first graphic object indicating the activation of the recording mode and a second graphic object indicating the extent to which the movement information on the wearer and the biological signal of the wearer are changed.

In the mobile terminal, the screen information may further include a third graphic object indicating time information corresponding to the activation of the recording mode and a fourth graphic object indicating the extent to which the movement information on the wearer and the biological signal of the wearer is matched with the already-stored movement pattern.

In the mobile terminal, in the recording mode, the controller may recognize repetition of the movement pattern that occurs in the specific situation and may further store accumulation information on and average information on the repeated movement patterns.

In the mobile terminal, in the recording mode or the control mode, the controller may control the display unit in such a manner that additional information associated with the accumulation information on and the average information on the repeated movement patterns is further displayed.

In the mobile terminal, when a second input signal is sensed in the specific situation, the controller may provide information corresponding to the movement information on the wearer and the biological signal of the wearer that are repeatedly recorded in the recording mode, to the connected external device.

The mobile terminal may further include a wireless communication unit that receives position information on the main body, in which in the control mode, the controller may receive the position information corresponding to changes in the movement information on the wearer and the biological signal of the wearer in the specific situation and may provide the received position information to the connected external device.

The mobile terminal may further include a display unit that is configured in such a manner that a first image indicating the activation of the control mode and a second image corresponding to the specific situation are output to the display unit in the control mode.

In the mobile terminal, in the control mode, the controller may recognize a gesture corresponding to the movement information and the biological signal that are sensed, may make a web search for at least one image associated with the recognized gesture, and may provide the searched-for image to the display unit.

The mobile terminal may further include a wireless communication unit that transmits image information to the connected external device, in which in the control mode, the controller may transfer to the connected external device the image information corresponding to at least one image associated with the recognized gesture.

In the mobile terminal, in the control mode, when a first signal responding to receiving of the control command corresponding to the movement pattern is received, the controller may output first screen information corresponding to the first signal to the display unit, and in the control mode, if a signal that checks the first screen information is input, when a second signal corresponding to a result of performing the control command is received from the connected external, the controller may output second screen information corresponding to the second signal to the display unit.

In the mobile terminal, in the control mode, when the already-stored movement pattern in a specific situation that corresponds to the movement information and the biological signal that are sensed is detected, the controller may control operation of the connected external device according to the control command that corresponds to the detected movement pattern, and in the control mode, when the already-stored movement pattern in the specific situation that corresponds to the movement information and the biological signal that are sensed is not detected, the controller may guide a user through entering of the recording mode.

In the mobile terminal, when the connection to the external device is established, the controller may provide state information on the wearer that corresponds to the biological signal of the wearer, to the external device, and when it is determined that the state information on the wearer is a state where the movement information cannot be input, the controller may perform control in such a manner that the external device operates according to the control command that is input in a different input manner.

In accordance with the purpose of this specification, as embodied and broadly described herein, there is provided a method of controlling a mobile terminal that is capable of connecting to at least one external device, the method including: sensing wearing of a main body; inputting a control command for activating either a recording mode or a control mode when the wearing of the main body is sensed; recording movement information on a wearer of the main body and a biological signal of the wearer in a specific situation and storing movement pattern that occurs in the specific situation, when the recording mode is activated; and sensing the movement information on the wearer and the biological signal of the wearer when the control mode is activated and providing a control command corresponding to the detected movement pattern and controlling the connected external device when the already-stored movement pattern in the specific situation that corresponds to the movement information and the biological signal that are sensed is detected.

The method may further include outputting screen information corresponding to the specific situation to a screen in the recording mode or the control mode.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal.

The foregoing embodiments are merely exemplary and are not to be considered as limiting the present disclosure. The present teachings can be readily applied to other types of methods and apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A mobile terminal comprising:
a main body;
a sensing module that senses whether the main body is being worn by a user, movement information of the user, and a biological signal of the user;
a user input module to receive a control command for activating either a recording mode or a control mode when the main body is sensed as being worn by the user; and
a controller configured to control the mobile terminal in the recording mode and the control mode, wherein
in the recording mode, the movement information on the user and the biological signal of the user in a prescribed situation is recorded, and a movement pattern that occurs in the prescribed situation is stored, and
in the control mode, the movement information on the user and the biological signal of the user is sensed, when the sensed movement information and the sensed biological signal correspond to the stored movement pattern for the prescribed situation, a control command corresponding to the stored movement pattern is provided to a connected external device, and
when the stored movement pattern for the prescribed situation that corresponds to the sensed movement information and the sensed biological signal is not detected in the control mode, the control mode is changed into the recording mode.

2. The mobile terminal of claim 1, wherein, when a first input signal is input and then movement information and the biological signal are sensed, a control command for activating the recording mode in a prescribed situation corresponding to the first input signal is generated, and
wherein, when the first input signal is input and then the movement information on the user and the biological signal of the user that exceed a reference value is sensed, a control command for activating the control mode is generated.

3. The mobile terminal of claim 2, wherein the first input signal is a sensing signal that corresponds to a connection between the user wearing the main body and the external device.

4. The mobile terminal of claim 2, wherein the prescribed situation is recognized based on at least one of the first input signal, ambient image information that is obtained through a camera provided on the main body, or position information of the main body that is received through a wireless communication module.

5. The mobile terminal of claim 1, wherein, when a connection between the main body and the external device is sensed, the control command for activating the recording mode or the control mode associated with the connected external device is provided to the user input module.

6. The mobile terminal of claim 5, wherein, when multiple external devices are connected to the main body, a prescribed external device to be controlled in the control mode is selected based on at least one of time information or ambient sound information associated with the connected external devices.

7. The mobile terminal of claim 1, further comprising:
a display module that displays screen information corresponding to the prescribed situation in the recording mode,
wherein the screen information includes a first graphic object indicating the activation of the recording mode and a second graphic object indicating the extent to which the movement information on the user and the biological signal of the user are changed.

8. The mobile terminal of claim 7, wherein the screen information further includes a third graphic object indicating time information corresponding to the activation of the recording mode and a fourth graphic object indicating the extent to which the movement information on the user and the biological signal of the user is matched with the stored movement pattern.

9. The mobile terminal of claim 1, wherein, in the recording mode, the controller recognizes repetition of the movement pattern that occurs in the prescribed situation and stores accumulation information and average information on the repeated movement patterns.

10. The mobile terminal of claim 9, wherein, in the recording mode or the control mode, the controller controls the display module to display additional information associated with the accumulation information and the average information on the repeated movement patterns.

11. The mobile terminal of claim 10, wherein, when a second input signal is sensed in the prescribed situation, information corresponding to the movement information on the user and the biological signal of the user that are repeatedly recorded in the recording mode are provided to the connected external device.

12. The mobile terminal of claim 1, further comprising a wireless communication module that receives position information of the main body,
wherein, in the control mode, the controller receives the position information corresponding to changes in the movement information on the user and the biological signal of the user in the prescribed situation and provides the received position information to the connected external device.

13. The mobile terminal of claim 1, further comprising a display module that is configured to display, in the control mode, a first image indicating the activation of the control mode and a second image corresponding to the prescribed situation.

14. The mobile terminal of 13, wherein, in the control mode, the controller recognizes a gesture corresponding to the movement information and the biological signal that are sensed, performs a web search for at least one image associated with the recognized gesture, and provides the searched-for image to the display module.

15. The mobile terminal of claim 1, further comprising:
a wireless communication module that transmits image information to the connected external device,
wherein, in the control mode, the image information corresponding to at least one image associated with the recognized gesture is transferred through the wireless communication module to the connected external device.

16. The mobile terminal of claim 1, wherein, in the control mode,
when a first signal is received in response to receiving the control command corresponding to the movement pattern, the controller displays on the display module first screen information corresponding to the first signal, and
when an input is received to confirm the first screen information, if a second signal corresponding to a result of performing the control command corresponding to the movement pattern is received from the connected external device, the controller displays on the display module second screen information corresponding to the second signal.

17. The mobile terminal of claim 1, wherein, in the control mode,
when the stored movement pattern for a prescribed situation that corresponds to the sensed movement information and the biological signal is detected, the controller controls operation of the connected external device according to the control command that corresponds to the detected movement pattern, and
when the stored movement pattern for the prescribed situation that corresponds to the sensed movement information and the biological signal is not detected, the controller provides a guide to guide the user through the recording mode.

18. The mobile terminal of claim 1, wherein, when the connection to the external device is established, state information on the user that corresponds to the biological signal of the user is provided to the external device, and
when the state information indicates that the user is in a state where the movement information cannot be input, the controller controls the external device based on a control command that is input in a different input manner.

19. A method of controlling a mobile terminal configured to connect to at least one external device, the method comprising:
sensing whether a main body of the mobile terminal is being worn by a user;
inputting a control command for activating either a recording mode or a control mode when the main body is sensed as being worn by the user;
recording movement information on a user of the main body and a biological signal of the user in a prescribed situation and storing a movement pattern that occurs in the prescribed situation when the recording mode is activated;
sensing the movement information on the user and the biological signal of the user when the control mode is activated, and when the sensed movement information and the sensed biological signal correspond to the stored movement pattern for the prescribed situation, providing a control command corresponding to the stored movement pattern to control the connected external device, and
when the stored movement pattern for the prescribed situation that corresponds to the sensed movement information and the sensed biological signal is not detected in the control mode, activating the recording mode.

20. The method of claim 19, further comprising outputting screen information corresponding to the prescribed situation to a display screen in the recording mode or the control mode.

* * * * *